(12) United States Patent
Pan et al.

(10) Patent No.: US 11,270,479 B2
(45) Date of Patent: Mar. 8, 2022

(54) OPTIMIZATION-BASED RECONSTRUCTION WITH AN IMAGE-TOTAL-VARIATION CONSTRAINT IN PET

(71) Applicants: KONINKLIJKE PHILIPS N.V., Eindhoven (NL); UNIVERSITY OF CHICAGO, Chicago, IL (US)

(72) Inventors: Xiaochuan Pan, Chicago, IL (US); Jinghan Ye, Livermore, CA (US); Amy Perkins, Philadelphia, PA (US); Chi-Hua Tung, Aurora, OH (US); Zheng Zhang, Chicago, IL (US)

(73) Assignees: KONINKLIJKE PHILIPS N.V., Eindhoven (NL); UNIVERSITY OF CHICAGO, Chicago, IL (US)

( * ) Notice: Subject to any disclaimer, the term of this patent is extended or adjusted under 35 U.S.C. 154(b) by 746 days.

(21) Appl. No.: 16/070,791

(22) PCT Filed: Feb. 13, 2017

(86) PCT No.: PCT/IB2017/050776
§ 371 (c)(1),
(2) Date: Jul. 18, 2018

(87) PCT Pub. No.: WO2017/149399
PCT Pub. Date: Sep. 8, 2017

(65) Prior Publication Data
US 2021/0209817 A1   Jul. 8, 2021

Related U.S. Application Data

(60) Provisional application No. 62/301,187, filed on Feb. 29, 2016.

(51) Int. Cl.
*A61B 6/00* (2006.01)
*G06T 11/00* (2006.01)
*A61B 6/03* (2006.01)

(52) U.S. Cl.
CPC ............ *G06T 11/006* (2013.01); *A61B 6/037* (2013.01); *A61B 6/4275* (2013.01); *A61B 6/461* (2013.01);
(Continued)

(58) Field of Classification Search
None
See application file for complete search history.

(56) References Cited

U.S. PATENT DOCUMENTS

2010/0124368 A1   5/2010   Ye
2011/0044546 A1   2/2011   Pan
(Continued)

FOREIGN PATENT DOCUMENTS

WO   2010/127241   11/2010
WO   2012/129140   9/2012
(Continued)

OTHER PUBLICATIONS

Liang, et al., "Implementation of non-linear filters for iterative penalized maximum likelihood image reconstruction" Nuclear Science Symposium Conference, 1990.
(Continued)

*Primary Examiner* — Hoon K Song

(57) ABSTRACT

In an emission imaging method, emission imaging data are acquired for a subject using an emission imaging scanner (10) including radiation detectors (12). The emission imaging data are reconstructed to generate a reconstructed image by executing a constrained optimization program including a measure of data fidelity between the acquired emission imaging data an a reconstruct-image transformed by a data model of the imaging scanner to emission imaging data. During the reconstructing, each iteration of the constrained optimization program is constrained by an image variability constraint. The reconstructed image is displayed the recon-
(Continued)

structed image on a display device. The emission imaging may be positron emission tomography (PET) imaging data, optionally acquired using a sparse detector array. The image variability constraint may be a constraint that an image total variation (image TV) of a latent image defined using a Gaussian blurring matrix be less than a maximum value.

24 Claims, 27 Drawing Sheets

(52) U.S. Cl.
CPC ............ *A61B 6/467* (2013.01); *A61B 6/5205* (2013.01); *G06T 2211/424* (2013.01)

(56) References Cited

U.S. PATENT DOCUMENTS

| | | | |
|---|---|---|---|
| 2011/0142316 A1 | 6/2011 | Wang | |
| 2013/0310678 A1 | 11/2013 | Balbi | |
| 2015/0287223 A1* | 10/2015 | Bresler | G06T 11/006 382/131 |
| 2015/0310653 A1* | 10/2015 | Knoll | G01R 33/5611 382/131 |
| 2015/0363947 A1 | 12/2015 | Rigie | |

FOREIGN PATENT DOCUMENTS

| | | |
|---|---|---|
| WO | 2013116709 | 8/2013 |
| WO | 2016011489 | 1/2016 |

OTHER PUBLICATIONS

Watson et al., "A single scatter simulation technique for scatter correction in 3d pet", in 3D Img. Recon. Radiol. Nucl. Med. Springer, 1996, pp. 255-268.

Badawi et al., "Randoms variance reduction in 3D PET", Phys. Med. Biol., vol. 44, No. 4, p. 941, 1999.

Chambolle and Pock, "A first-order primal-dual algorithm for convex problems with applications to imaging", J. Math. Imag. Vis., vol. 40, p. 1 26, 2011.

Browne et al., "A row-action alternative to the EM algorithm for maximizing likelihood in emission tomography", IEEE Trans. Med. Imag., vol. 15.5, p. 687 99, 1996.

Zhang, et al., "Investigation of optimization-based reconstruction with an image-total-variation constraint in PET" Physics in Medicine & Biology, vol. 61, No. 16.

Burger, et al., "A Nonlinear Variational Approach to Motion-Corrected Reconstruction of Density Images" 2015.

Sidky, et al., "Convex optimization problem prototyping with the Chambolle-Pock algorithm for image reconstruction in computed tomography" Phys Med Biol. May 21, 2012; 57(10): 3065-3091.

Kaganovski, et al., "Alternating minimization algorithm with automatic relevance determination for transmission tomography under Poisson noise" Jan. 2015.

Bian, et al., "Optimization-based Image Reconstruction from Sparse-view Data in Offset-Detector CBCT", Phys Med Biol. Jan. 21, 2013; 58(2): 205-230.

* cited by examiner $\hat{u}^*, t_0=6225$    $\hat{u}^*, t_0=10375$    $\hat{u}^*, t_0=13488$    $\hat{u}^*, t_0=17638$    $\hat{u}^*, t_0=25938$

OPTIMIZATION-BASED RECONSTRUCTION WITH AN IMAGE-TOTAL-VARIATION CONSTRAINT IN PET

CROSS REFERENCE TO RELATED APPLICATIONS

This application is the U.S. National Phase application under 35 U.S.C. § 371 of International Application No. PCT/IB2017/050776 filed Feb. 13, 2017, published as WO 2017/149399 on Sep. 8, 2017, which claims the benefit of U.S. Provisional Patent Application No. 62/301,187 filed Feb. 29, 2016. These applications are hereby incorporated by reference herein.

This invention was made with Government support under grants CA158446, CA182264, and EB018102 awarded by the National Institutes of Health (NIH). The Government has certain rights in this invention.

FIELD

The following relates generally to the medical imaging arts, positron emission tomography (PET) arts, image reconstruction arts, and the like.

BACKGROUND

Image reconstruction is a key component in the development and application of advanced positron-emission tomography (PET) imaging. Some known PET image reconstruction algorithms have been developed based upon expectation-maximization (EM), row-action maximum-likelihood (RAMLA), maximum a posteriori (MAP), and penalized maximum-likelihood (PML) algorithms. The algorithms have also been extended to list-mode, time-of-flight (TOF) PET imaging, and 4D spatial-temporal/parametric image reconstructions. Notwithstanding the foregoing, further improvement in image quality in PET imaging would be advantageous. Such improvements may, for example, enable use of PET detection and electronic technologies with reduced density of detectors without (or with reduced) concomitant loss in image quality. The ability to reduce the density of detectors while (at least substantially) retaining image quality would enable reduction in PET imaging device cost and could also provide benefits such as more efficient data processing due to the reduced data set sizes being reconstructed.

The following discloses a new and improved systems and methods that address the above referenced issues, and others.

SUMMARY

In one disclosed aspect, an emission imaging device comprises an emission imaging scanner including radiation detectors for acquiring emission imaging data, an electronic data processing device programmed to reconstruct emission imaging data acquired by the emission imaging scanner to generate a reconstructed image, and a display device connected to display the reconstructed image. The emission imaging data are reconstructed to generate the reconstructed image by executing a constrained optimization program that is constrained by an image variability constraint $\|T(u)\| \leq t_0$ in which $t_0$ is an image variability constraint parameter, u is the reconstructed image at a current iteration of the constrained optimization program, T(u) is a sparsifying image transform, and $\|\ldots\|$ is a norm that outputs a strictly positive scalar value for the transformed image T(u).

In another disclosed aspect, an emission imaging method comprises: acquiring emission imaging data $g_m$ for a subject using an emission imaging scanner including radiation detectors; reconstructing the emission imaging data to generate a reconstructed image by executing the optimization program $$u^* = \operatorname*{argmin}_u D(g_m, g(u))$$

where g(u) denotes a data model of the emission imaging scanner that transforms the reconstructed image u at the current iteration of the optimization program into emission imaging data and $D(g_m, g(u))$ denotes a measure of data fidelity between the $g_m$ and g(u); during the reconstructing, constraining each iteration of the optimization program by an image variability constraint $\|T(u)\| \leq t_0$ in which $t_0$ is an image variability constraint parameter, T(u) is a sparsifying image transform, and $\|\ldots\|$ is a norm that outputs a strictly positive scalar value for the transformed image T(u); and displaying the reconstructed image on a display device.

In another disclosed aspect, a positron emission tomography (PET) imaging device comprises: a PET scanner including an annular ring of radiation detectors for acquiring PET imaging data; an electronic data processing device (20) programmed to reconstruct PET imaging data acquired by the PET scanner to generate a reconstructed image; and a display device (34) connected to display the reconstructed image. The PET imaging data are reconstructed to generate the reconstructed image by executing a constrained optimization program:

$$u^* = \operatorname*{argmin}_u D(g_m, g(u)) \text{ subject to } \|f\|_{TV} \leq t_0 \text{ and } f_j \geq 0$$

where g(u) denotes a data model of the PET scanner that transforms the reconstructed image u at the current iteration of the constrained optimization program into emission imaging data, $D(g_m, g(u))$ denotes a measure of data fidelity between the $g_m$ and g(u), $\|f\|_{TV} \leq t_0$ is an image total variation constraint in which $t_0$ is a total variation constraint parameter and f is a latent image defined by $u = \mathcal{G}f$ where $\mathcal{G}$ is a blurring matrix which is not an identity matrix, and $f_j \geq 0$ is a positivity constraint.

One advantage resides in providing PET imaging with reduced equipment cost by enabling the use of a reduced number of crystals and associated electronics.

Another advantage resides in providing more efficient PET reconstruction via acquisition of smaller PET imaging data sets.

Another advantage resides in providing either one or both of the foregoing advantages without a concomitant degradation in clinical value of the PET images.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
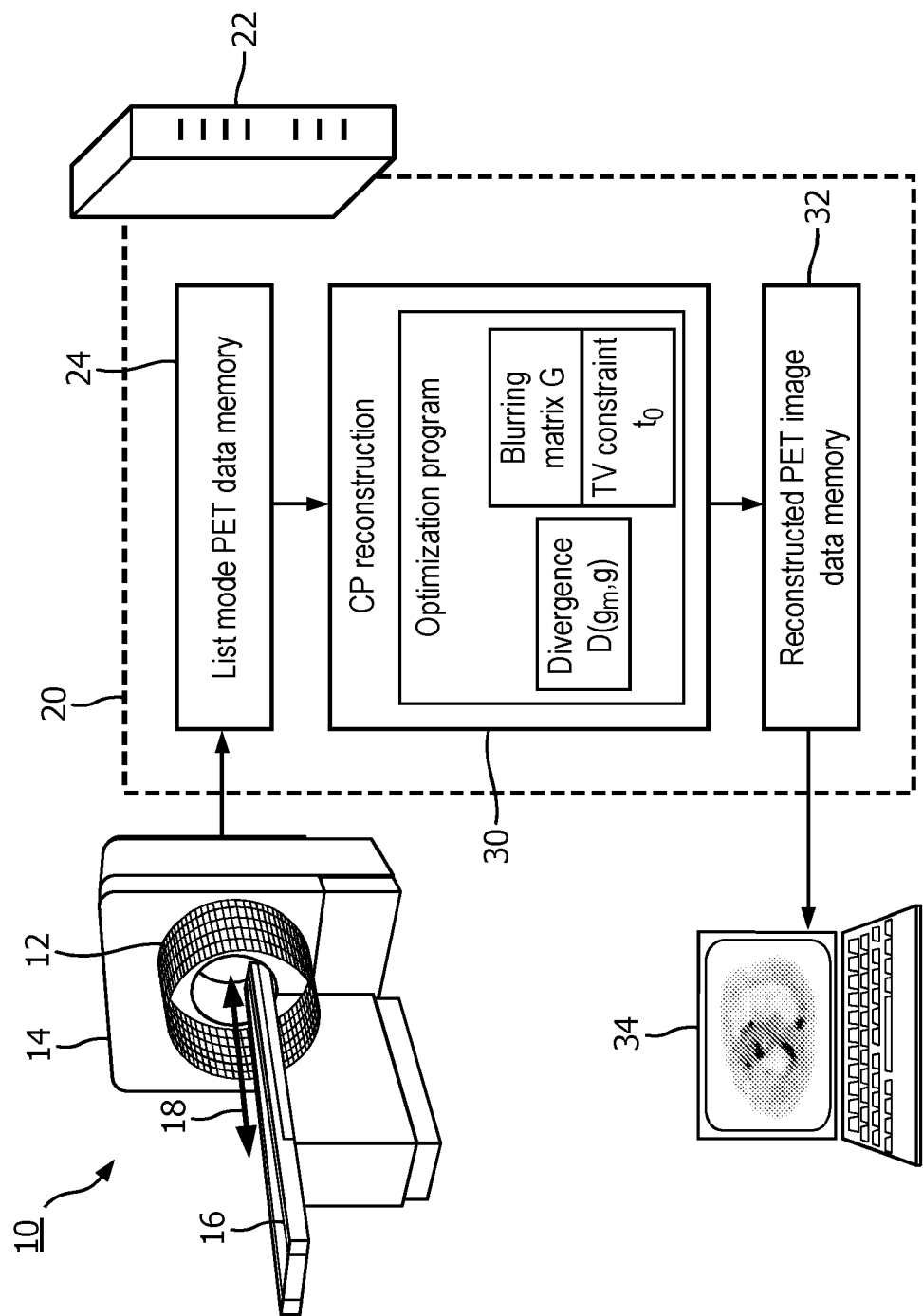
FIG. 1 diagrammatically shows a positron emission tomography (PET) imaging system.

With reference to FIG. 1, a positron emission tomography (PET) imaging system includes a PET scanner 10 including one or more annular rings of PET detectors 12 mounted in a suitable housing 14, with a patient support 16 arranged to move a patient along an axial direction 18 oriented generally transverse to the plane of the rings 12. Note that while diagrammatic FIG. 1 shows the PET detector ring(s) 12 in the housing 14, more typically the housing is opaque and would occlude the PET detectors from view. Further, while the illustrative PET scanner 10 is a standalone device, PET reconstruction algorithms disclosed herein are equally applicable to hybrid imaging systems with a PET component, such as a computed tomography (CT)/PET scanner.

When used for medical imaging, a radiopharmaceutical is administered to a human imaging subject, and the subject is disposed on the support 16 and moved into the PET rings 12. The radiopharmaceutical includes radioisotopes that produce positrons during radioactive decay events, and each positron annihilates with an electron in a positron-electron annihilation event that outputs two oppositely directed 511 keV gamma rays. PET imaging data are acquired by the PET detectors 12 in the form of gamma ray detection event, which may be stored in a list mode format in which each event is time stamped.

In illustrative FIG. 1, an electronic data processing device 20 processes the PET data to generate a reconstructed image. The illustrative electronic data processing device 20 is a computer 22, e.g. a server computer, desktop computer, a cloud computing resource, or the like. The list mode data are stored in a list mode PET data memory 24 (e.g. hard drive, RAID disk, solid state drive, et cetera) which is a component of, or accessible by, the device 20. The list mode data are filtered to retain events within a window about 511 keV (energy filtering) and to identify substantially simultaneous events attributable to positron-electron annihilation events (coincidence detection). Such a pair defines a line of response (LOR) between the two simultaneous detection events. Some detected events are not due to positron-electron annihilation events, but rather are random events. Some detected events may be due to positron-electron annihilation events, but one or both 511 keV gamma rays may have undergone scattering so that the pair no longer defines a true LOR these are called scattering events. A reconstruction processor 30 processes the filtered list mode data to generate a reconstructed PET image that is stored in an image data memory 32 (e.g. hard drive, RAID disk, solid state drive, et cetera) which is a component of, or accessible by, the device 20. Various suitable reconstruction algorithms that may be implemented by the reconstruction processor 30 are described herein. The reconstructed image may be displayed on a display device 34, e.g. a computer LCD display component of a workstation, desktop computer, notebook computer, or the like.

In the following, some illustrative embodiments of reconstruction algorithms that may be implemented by the reconstruction processor 30 are described.

Figure 1A:
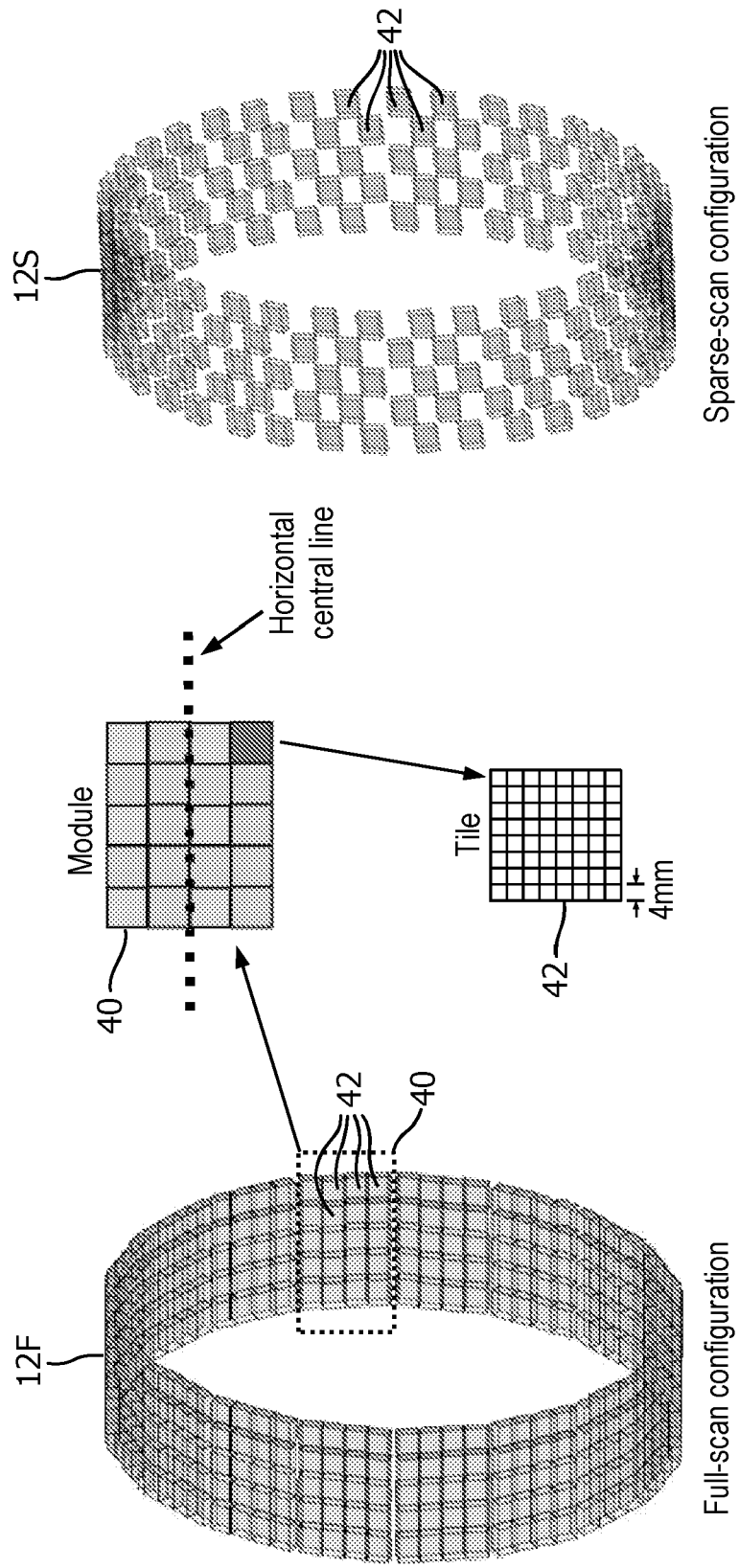
FIG. 1A shows a full-scan PET detector array and a sparse-scan PET detector array.

With reference to FIG. 1A, a full-scan PET detector array 12F suitably used as the PET ring 12 of FIG. 1 is shown. The PET detector array 12F is formed by tightly assembling P identical detector modules 40, each of which itself is a flat panel containing L×K identical tiles 42 of square shape, on a cylindrical surface of radius R. In particular, the centers of the modules 40 are placed on the same circular ring on the cylindrical surface, while the horizontal central lines of the modules 40 are parallel to the central axis of a cylindrical surface. Therefore, the full-scan configuration consists effectively of L rings of P×K tiles. Each of the tightly congregated tiles itself within a module is composed of J×J identical crystal bins of square shape and length d. A straight line connecting the centers of two crystal detector-bins forms a line-of-response (LOR) along which a data sample is collected. A PET configuration with M distinct LORs thus yields a data set of at most M samples. In the work, this configuration is referred to as the full-scan configuration, and data collected with the configuration the "full data".

In the Monte-Carlo-simulation and real-data studies described herein, PET data were collected by use of the full PET detector configuration 12F of FIG. 1A, in a digital prototype PET/CT system, identical to that described above, with P=18, L=5, K=4, J=8, and d=4 mm, yielding a total of M=153,446,400 distinct LORs. Also investigated was image reconstruction from data collected from a sparse-scan PET detector array configuration 12S also shown in FIG. 1A, that is formed by removing odd- or even-numbered tiles 42 in odd- or even-numbered rings in the full-scan configuration 12F. The sparse-scan configuration 12S thus includes L rings each of which is composed only of P/2×K uniformly, but sparsely, distributed tiles 42, as depicted in FIG. 1A for the sparse PET detector array 12S. Data collected with the sparse-scan configuration is referred to herein as "sparse data". It can be shown that the sparse-scan configuration has a total of M=38,361,600 possible distinct LORs (i.e. line of response paths). The sparse-scan configuration 12S is representative of an approach for PET imaging with a considerably reduced number of crystals and associated electronics (relative to the full-scan configuration 12F). The clinically useful image reconstruction of sparse data sets as described herein thus facilitates PET imaging with reduced equipment costs. Processing of the sparse data set also is more computationally efficient since, for a given radiopharmaceutical dose and acquisition time, the sparse data set is smaller than the equivalent full data set.

The following notation is used in illustrative examples herein. discrete image is defined on a three-dimensional (3D) array containing $N=N_x \times N_y \times k$ identical voxels of cubic shape, where $N_x$, $N_y$, and $N_z$ denote the numbers of voxels along the Cartesian x-, y-, and z-axis, respectively. The z-axis coincides with the central axis of the PET configuration 12F (or 12S) shown in FIG. 1A, which is the axial direction 18 labeled in FIG. 1. We use vector u of size N to denote the image in a concatenated form. The PET-data model used in the study (that is, the data model of the emission imaging scanner 10 that transforms the image u into emission imaging data) is given by:

$$g(u) = \mathcal{H}_{u+g_s+g_r} \quad (1)$$

where vector g(u) of size M denotes the model data, $\mathcal{H}$ is an M×N system matrix in which element $h_{ij}$ is the intersection length of LOR i with voxel j, vectors $g_s$ and $g_r$ of size M denote scatter and random events, which are assumed to be known in the work. In the following, the notation g is generally used as a shorthand for g(u). We use vector $g_m$ of size M to denote the measured data. In this work, $g_m$, $g_s$, and $g_r$ are corrected for the effect of photon attenuation. The goal of PET-image reconstruction is to determine (i.e., reconstruct) u from knowledge of $g_m$, $\mathcal{H}$, $g_s$, and $g_r$.

Using Equation (1), we form an optimization program in the form of:

$$u^* = \operatorname*{argmin}_{u} D(g_m, g) \text{ s.t. } \|f\|_{TV} \le t_0 \text{ and } f_j \ge 0 \qquad (2)$$

where $D(g_m,g)$ denotes a measure of data fidelity between measured data $g_m$ and model data g, and "s.t." is standard notation indicating "subject to" the constraint that follows.

One constraint in Equation (2) is a positivity constraint, i.e. $f_j \ge 0$, which ensures that the voxels of latent image f have positive values. The other constraint is an image total variation (TV) constraint. The image TV norm $\|f\|_{TV}$ in this image TV constraint may be defined as:

$$\|f\|_{TV} = \sum_{x,y} |\vec{\Delta} f_{x,y}| = \sum_{x,y} \sqrt{(f_{x,y} - f_{x-1,y})^2 + (f_{x,y} - f_{x,y-1})^2} \qquad (2a)$$

where x and y denote pixel labels or, for a three-dimensional (3D) image:

$$\|f\|_{TV} = \sum_{x,y,z} |\vec{\Delta} f_{x,y,z}| = \sum_{x,y,z} \sqrt{\begin{array}{c}(f_{x,y,z} - f_{x-1,y,z})^2 + (f_{x,y,z} - f_{x,y-1,z})^2 + \\ (f_{x,y,z} - f_{x,y,z-1})^2\end{array}} \qquad (2b)$$

It will be appreciated that the image TV norm may be written with other handedness, e.g. the "−1" operations in the subscripts may be replaced by "+1" operations.

The image u to be reconstructed is related to latent image vector f of size N through:

$$u = \mathcal{G} f \qquad (3)$$

In Equation (3), $\mathcal{G}$ a matrix of size N×N, $\|f\|_{TV}$ is the image total variation norm of f and is constrained by the total variation (TV) constraint parameter $t_0$, $f_j$ the jth element of vector u, and j=1, 2, . . . , N.

In some tested illustrative reconstruction algorithms, the blurring matrix $\mathcal{G}$ was obtained as follows. For a three-dimensional (3D), isotropic Gaussian function centered at a given voxel in the image array, we calculate its values at the center locations of N voxels within the image array, and use the calculated values in a concatenated form identical to that of vector u to create a vector of size N. Repeating the calculation for each of the N voxels in the image array, N such vectors can be formed; and matrix $\mathcal{G}$ of size N×N can subsequently be built in which a row is the transpose of one of the N vectors, and the N rows are in an order consistent with the concatenated order of entries of u. The unit of standard deviation of the Gaussian function is defined in terms of voxel size. With standard deviation taking zero value, $\mathcal{G}$ reduces to the trivial case of the identity matrix $\mathcal{I}$. (That is, in some embodiments it is contemplated to replace the Gaussian blurring matrix or blurring operator $\mathcal{G}$ with the identity matrix so that Equation (3) becomes u=f). Other blurring operators, e.g. with other than an identity matrix or Gaussian form, are also contemplated).

In illustrative reconstruction algorithms, three specific implementations of the "generic" divergence $D(g_m,g)$ of Equation (2) were tested.

The first tested divergence was the Kullback-Leibler (KL) divergence, for which the program of Equation (2) becomes:

$$u^* = \operatorname*{argmin}_{u} D_{KL}(g_m, g) \text{ s.t. } \|f\|_{TV} \le t_0 \text{ and } f_j \ge 0 \qquad (4)$$

where $D_{KL}(g_m,g)$ denotes the data-KL divergence given by:

$$D_{KL}(g_m, g) = \sum_{i}^{M} [g - g_m + g_m \ln g_m - g_m \ln g]_i \qquad (4a)$$

where $[\bullet]_i$ denotes the ith element of vector $[\bullet]$. When computing $D_{KL}$, $(g_m,g)$ in experiments reported herein, the entries in g that are smaller than $\varepsilon = 10^{-20}$ are replaced with $\varepsilon$. For the convenience of devising convergence conditions below, a normalized data-KL divergence is defined as $D'K_L (g_m,g)=D_{KL}(g_m,g)/D_{KL}(g_m,g_\varepsilon)$, where $g_\varepsilon$ is obtained by replacing all of the entries in g with $\varepsilon$. We refer to the optimization program in Equation (4) as program "DKL-fTV".

The second tested divergence employed the $\ell_2$-norm. The program of Equation (2) becomes:

$$u^* = \operatorname*{argmin}_{u} D_{\ell_2}(g_m, g) \text{ s.t. } \|f\|_{TV} \le t_0 \text{ and } f_j \ge 0 \qquad (5)$$

which is obtained by the replacement of $D(g_m,g)$ in Equation (2) with:

$$D_{\ell_2}(g_m,g) = \|g_m - g\|_2 \qquad (5a)$$

This fidelity metric takes the $\ell_2$-norm of the difference between the measured data and model data. Also, for the convenience of specifying convergence conditions below, a normalized data-$\ell_2$ is defined as $D'_{\ell_2}(g_m,g) = D_{\ell_2}(g_m,g)/D_{\ell_2}(g_m,0)$. We refer to the optimization program in Equation (5) as the program "DL2-fTV".

The third tested divergence employed the $\ell_1$-norm. The program of Equation (2) becomes:

$$u^* = \operatorname*{argmin}_{u} D_{\ell_1}(g_m, g) \text{ s.t. } \|f\|_{TV} \le t_0 \text{ and } f_j \ge 0 \qquad (6)$$

which is obtained by the replacement of $D(g_m,g)$ in Equation (2) with:

$$D_{\ell_1}(g_m,g) = \|g_m - g\|_1 \qquad (6a)$$

denoting the $\ell_1$-norm of difference between measured data and model data. Again, for the convenience of describing convergence conditions below, a normalized data-$\ell_1$ is defined as $D'_{\ell_1}(g_m,g) = D_{\ell_1}(g_m,g)/D_{\ell_1}(g_m,0)$. We refer to the optimization program in Equation (6) as the program "DL1-fTV".

In an optimization-based reconstruction, numerous parameters are employed to specify explicitly the program, i.e., the solution set, which are referred to as "program parameters". We consider "algorithm parameters" to be those that affect only algorithm's convergence path leading to the solution set, and thus have no impact on the theoretical specification (or design) of the solution set. Clearly, the solution set depends upon the specific form of the optimization program, and thus the optimization program itself constitutes a program parameter. Moreover, an optimization program of a given form itself involves additional program parameters. For the optimization programs considered in Equations (4)-(6), additional program parameters include system matrix $\mathcal{H}$, scatter and random components $g_s$ and $g_r$, the voxel size, TV-constraint parameter $t_0$, and blurring matrix $\mathcal{H}$.

The optimization algorithms used in experiments disclosed herein can solve the convex optimization programs of Equations (4)-(6), but like any other iterative algorithms, they only converge to a solution in the limit of infinite iterations. Due to the limitation of computer precision and computation time, one can obtain reconstructions only at finite iterations. Therefore, practical convergence conditions are specified under which reconstructions can be achieved within a finite number of iterations; and the practical convergence conditions thus play a role in defining an actual solution set achievable within a finite number of iterations. In experiments reported herein, when the practical conditions are satisfied, the reconstruction stops and is referred to as the "convergent reconstruction" û*; and we also denote the corresponding latent image as f̂*, where û* = $\mathcal{G}$f̂*.

As already described, system matrix $\mathcal{H}$ contains M row vectors of size N in which each entry depicts the intersection of an LOR with a voxel in the image array. In the validation and Monte-Carlo-simulation studies reported herein, scatter and random events $g_s$ and $g_r$ are not considered; whereas in the phantom and human imaging studies reported herein, the single-scatter simulation method (Watson et al., "A single scatter simulation technique for scatter correction in 3d pet", in 3D Img. Recon. Radiol. Nucl. Med. Springer, 1996, pp. 255-68) and the delayed coincidence method (Badawi et al., "Randoms variance reduction in 3D PET", Phys. Med. Biol., vol. 44, no. 4, p. 941, 1999) were employed for estimating $g_s$ and $g_r$, respectively. A voxel size of 4 mm was selected for the studies because it is used often in clinical studies. Blurring matrix $\mathcal{G}$ generated by use of a 3D isotropic Gaussian function with a standard deviation of 2.4 mm, which is 0.6 times the image-voxel size, appears to yield appropriate reconstructions for data conditions considered.

For designing the practical convergence conditions, we introduce two unitless metrics as:

$$CTV(f_n) = |\|f_n\|_{TV} - t_0|/t_0 \tag{7}$$

and $$D'(u_n) = D(g_m, g_n)/D(g_m, 0) \tag{8}$$

where $u_n$ and $f_n$ denote reconstructions at iteration n, $g_n = \mathcal{H} u_n + g_s + g_r$ the model data estimated at the nth iteration, obtained by replacing u with $u_n$ in Equation (1). Practical convergence conditions are devised with $CTV(f_n)$ and $D'(u_n)$ for the studies performed herein.

With the program parameters and practical convergence conditions specified above, only image-TV-constraint parameter $t_0$ remains to be determined. We discuss the determination of $t_0$ in each specific study carried out below, because different data conditions in the studies can have considerably different impacts on the appropriate selection of $t_0$.

Optimization programs DKL-fTV, DL2-fTV, and DL1-fTV in Equations (4)-(6) are convex, and can be solved with a number of existing algorithms. Experiments reported herein utilize algorithms belonging to a class of algorithms known as the primal-dual algorithms.

A specific set of first-order, primal-dual algorithms developed by Chambolle and Pock (CP) (Chambolle and Pock, "A first-order primal-dual algorithm for convex problems with applications to imaging", J. Math. Imag. Vis., vol. 40, pp. 1-26, 2011) has been demonstrated to be an effective investigative tool for solving a variety of convex optimization programs in CT imaging, including the convex programs having the form of Equations (4)-(6). Pseudo-code for the CP algorithm is given below:

Algorithm: Pseudo-code for $\mathcal{N}$ steps of the CP algorithm for solving Eq. (4)-(6)

1:     INPUT: measured events $g_m$, scatter events $g_s$, random events $g_r$, TV constraint parameter $t_0$, Gaussian blurring operator $\mathcal{G}$
2:     INPUT: parameter $\lambda$
3:     $v = \|\mathcal{HG}\|_{SV}/\|\nabla\|_{SV}$, $c = vt_0$
4:     $L \leftarrow \|(\mathcal{HG}, \nabla)\|_{SV}$
5:     $\tau \leftarrow 1/\lambda L$; $\sigma \leftarrow \lambda/L$; $\theta \leftarrow 1$; $n \leftarrow 0$
6:     INITIALIZE: $f_0, u_0, y_0$, and $\vec{z}_0$ to zero
7:     $\bar{f}_0 \leftarrow f_0$
8:     while Not done do
9:         $y_{n+1} = \Phi(y_n, \bar{g}_n, g_m)$
10:       $\vec{t} = \vec{z}_n + \sigma v \nabla \bar{f}_n$
11:       $\vec{z}_{n+1} = (1 - \sigma\text{ProjectOnto}\ell_1\text{Ball}_c(|\vec{t}|/\sigma)/|\vec{t}|)\vec{t}$
12:       $f_{n+1} = \text{pos}(f_n - \tau(\mathcal{G}^T\mathcal{H}^T y_{n+1} + v\nabla^T \vec{z}_{n+1}))$
13:       $u_{n+1} = \mathcal{G} f_{n+1}$
14:       $\bar{f}_{n+1} = f_{n+1} + \theta(f_{n+1} - f_n)$
15:       $n \leftarrow n + 1$
16:    end while
17:    OUTPUT: image $\hat{u}^* = u_\mathcal{N}$ In this algorithm, $\nabla$ depicts a matrix representing a finite differencing approximation of the image gradient, yielding vectors $\nabla f$, $\vec{t}$, and $\vec{z}_n$ N-element vectors with each entry a vector of size 3, norm $\|\bullet\|_{SV}$ of a linear operator computes the largest singular value of that linear operator, $\bar{g}_n = \mathcal{HG}\bar{f}_n + g_s + g_r$, $|\vec{t}|$ denotes an N-element vector by taking the magnitude of each entry of $\vec{t}$, operator [ProjOnto $\ell_1\text{Ball}_c$] yields a vector of size N by projection of vector $|\vec{t}|/\sigma$ onto the $\ell_1$-ball of scale c, the multiplication of $\vec{t}$ and $(1-\sigma\text{ProjectOnto}\ell_1\text{Ball}_c(|\vec{t}|/\sigma)/|\vec{t}|)$ in Line 11 is performed component-wise, and superscript "T" transpose operation. Operator pos(•) enforces non-negativity of the all entries of the input vector. Algorithm parameter $\lambda$ can affect the convergence path and rate of the CP algorithms especially at early iterations. For the studies reported herein, $\lambda = 0.01$ was used because it has been shown in the study to yield a reasonable convergence rate at early iterations.

We note that all of the lines in the pseudo-code are identical for the three optimization programs in Equations (4)-(6), except for vector $\Phi$ of size M in line 9, which may vary depending upon the specific data divergence considered. For the program in Equation (4):

$$\Phi(y_n, \bar{g}_n, g_m) = \tfrac{1}{2}[1_D + y_n + \sigma \bar{g}_n] - \sqrt{(1_D - y_n - \bar{g}_n)^2 + 4\sigma g_m} \tag{9}$$

where $1_D$ is a vector of size M filled with 1s. For the optimization program in Equation (5):

$$\Phi(y_n, \bar{g}_n, g_m) = [y_n + \sigma(\bar{g}_n - g_m)]/(1+\sigma) \tag{10}$$

and for the optimization program in Equation (6):

$$\Phi(y_n, \bar{g}_n, g_m) = \frac{y_n + \sigma(\bar{g}_n - g_m)}{\max(1_D, |y_n + \sigma(\bar{g}_n - g_m)|)} \quad (11)$$

where max(•) is performed element-wise.

Reconstruction techniques based upon the Row-action maximum-likelihood algorithm (RAMLA) (Browne et al., "A row-action alternative to the EM algorithm for maximizing likelihood in emission tomography", IEEE Trans. Med. Imag., vol. 15.5, pp. 687-99, 1996) are used frequently in PET image reconstruction. RAMLA can be viewed as a relaxed ordered-subset algorithm in which the step size is subset-independent and gradually decreases to zero. Under certain conditions, the RAMLA algorithm is mathematically equivalent to the Expectation-Maximization (EM) algorithm, but they involve different implementation procedures and can lead to different solutions when a finite number of iterations are used as in all practical reconstructions.

In experiments reported herein, the RAMLA algorithm was applied to reconstructing from full data PET images $u_{ref}$, and the full data RAMLA reconstructions were used as reference reconstructions for comparative purposes. Specifically, the RAMLA implementation in the study consists of subsets with the number of LORs varying from 291 to 291×40, and yields the reconstruction after two full iterations, as is done typically in practical research and clinical applications. RAMLA reconstructions from sparse data were also carried out in each of the studies described below, and were observed to have quality substantially lower than that of the reference reconstructions. Therefore, the RAMLA reconstructions of sparse data are not illustrated herein.

For the purpose of validation and computation-efficiency consideration, we used the full-scan configuration 12F of FIG. 1A, but with only one ring of tiles, and a 3D image array consisting of 50×50×8 identical cubic voxels of size 4 mm. With the configuration and image array given, system matrix $\mathcal{H}$, and Gaussian matrix $\mathcal{G}$ can be formed as already described.

Figure 2:
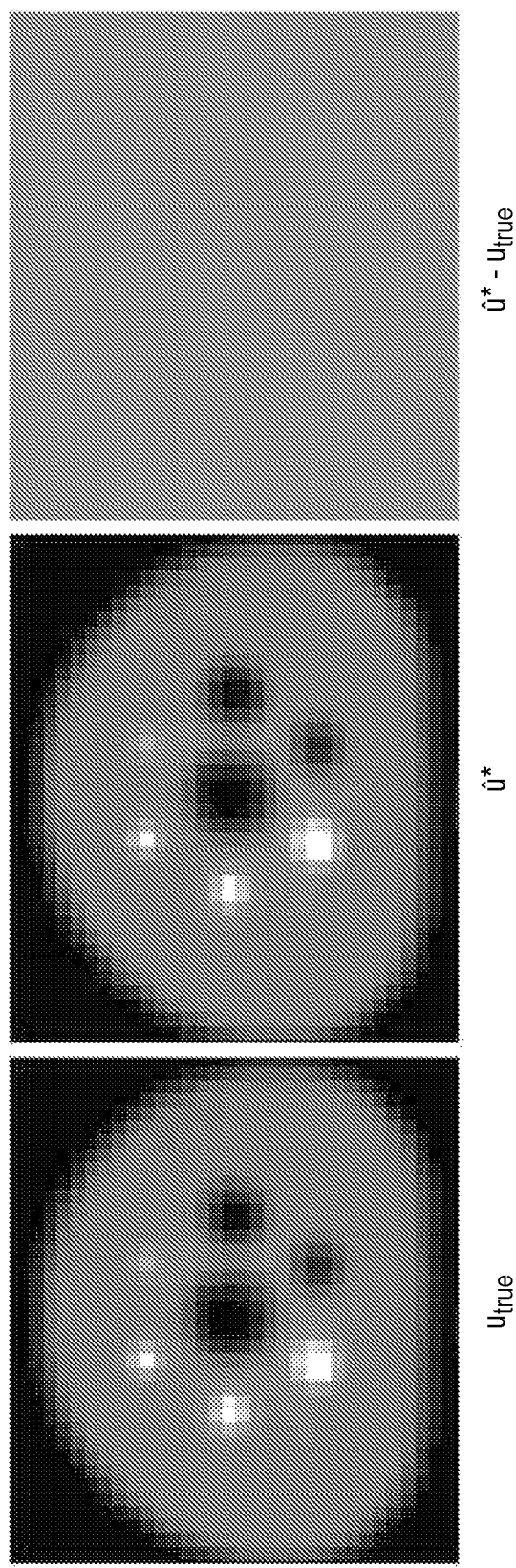
FIGS. 2-24 present simulation and experimental results as described herein.

FIG. 2 shows a truth image $u_{true}$, a convergent reconstruction $\hat{u}^*$, and difference $\hat{u}^* - u_{true}$. Display window [0.0, 0.1] is used for the truth image and reconstruction, and display window [−0.0001, 0.0001] is used for their difference. Image values are in arbitrary units. In accord with Equation (3), we create truth image $u_{true}$ shown in FIG. 2 (left image) by application of matrix $\mathcal{G}$ to a known, numerical IEC (International Electrotechnical Commission) phantom $f_{true}$, i.e., the truth latent image. Subsequently, model data g is generated from $u_{true}$ by use of system matrix $\mathcal{H}$. Without loss of generality, random and scatter are not considered (i.e., $g_s=0$ and $g_r=0$) in the study.

The mathematical convergence conditions for the CP algorithms include $CTV(f_n) \to 0$, $D'(u_n) \to 0$, and $cPD(u_n) \to 0$, as $n \to \infty$, where cPD $(u_n)$ denotes the conditional primal-dual (cPD) gap. They are unachievable, however, due to limited computer precision and computation time involved in any practical, numerical study. Therefore, for the inverse-crime study considered, we designed practical convergence conditions, namely:

$CTV(f_n) < 10^{-5}$ $D'(u_n) < 10^{-5}$ $cPD(u_n) < 10^{-3}$ \quad (12)

and require that the convergence metrics maintain their decaying trends even after that the conditions are satisfied, as n increases, where $D'(u_n) = D'_{KL}(u_n)$, $D'_{\ell_2}(u_n)$, and $D'_{\ell_1}(u_n)$, respectively, for optimization programs in Equations (4), (5), and (6). Practical convergence conditions that are tighter or looser than those in Equation (12) can readily be designed, depending upon the amount of computation resources to be invested.

In the following, we report performed inverse-crime studies on reconstructions based upon the three optimization programs in Equations (4)-(6) in which $t_0 = \|f_{true}\|_{TV}$ is computed from truth-latent-image $f_{true}$. For brevity, we show results obtained only for program DKL-fTV in Equation (4), as similar results were obtained also for programs in Equations (5) and (6). It can be observed in FIG. 2 that convergent reconstruction $\hat{u}^*$ (middle image) is visually virtually identical to truth image $u_{true}$ (left image).

Figure 3:
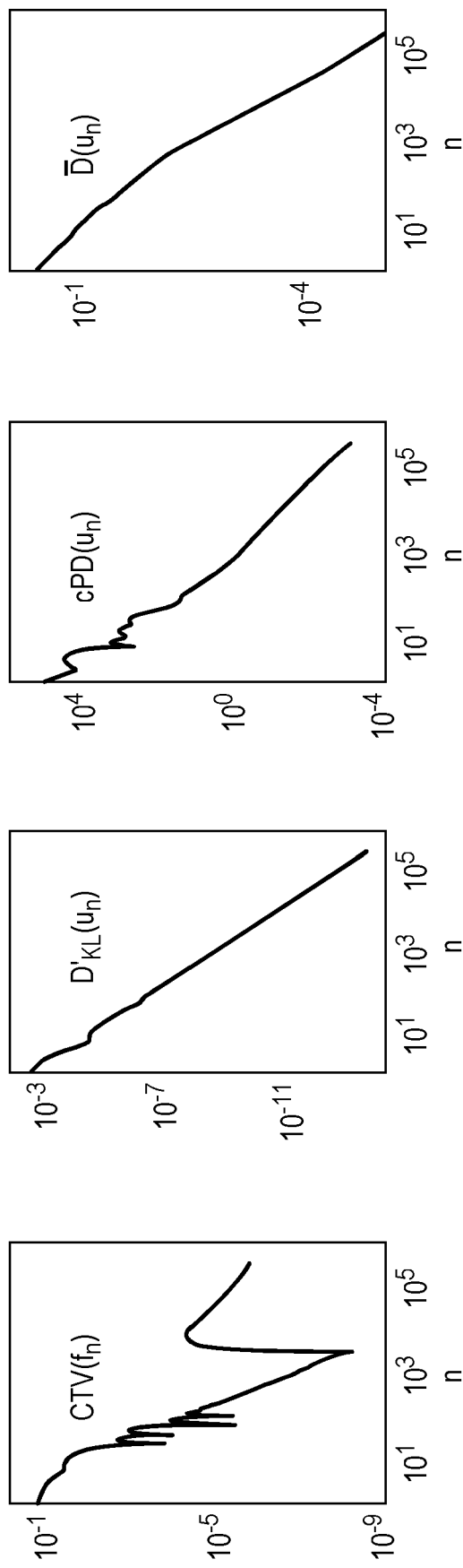

FIG. 3 shows convergence metrics $CTV(f_n)$, $D'_{KL}(u_n)$, $cPD(u_n)$ as functions of iteration number n. FIG. 3 shows how convergence metrics evolve as functions of the iteration number, demonstrating that the practical convergence conditions in Equation (12) are satisfied. Because $u_{true}$ is known, we also calculated $$\bar{D}(u_n) = \frac{\|u_n - u_{true}\|_2}{\|u_{true}\|_2},$$

and display it also in FIG. 3 (rightmost plot), which indicates that the reconstruction converges to the truth image. Furthermore, it can be observed that the convergent metrics maintain their decaying trends beyond the convergence conditions in Equation (12). Therefore, the results of the inverse-crime study numerically assure the correct computer implementation of the CP algorithms.

In the studies reported in the following, we designed practical convergence conditions:

$CTV(f_n) < 10^{-5}$ $D'(u_n) \to$ plateau \quad (13)

as n increases. The convergence conditions of Equation (13) are less restrictive than those in Equation (12) for the inverse-crime study, and they are designed based upon the practical considerations: (a) in a real-data study, because inconsistency exists between measured data $g_m$ and model data g, $D'(u) > 0$ is generally non-zero; and because full knowledge is unavailable about model data g, the value of $D'(u)$ is generally unknown. Therefore, condition $D'(u_n) \to$ plateau, instead of $D'(u_n) \to 0$, is considered. Unlike metrics $CTV(f)$ and $D'(u)$ that provide directly meaningful measures of physical properties of reconstructions in a practical study, metric cPD $(u_n)$ yields a mathematical check on the correctness of the algorithm implementation. Consequently, once the implementation correctness is verified in the inverse-crime study, metric cPD $(u_n)$ is not used in real-data studies in which practical convergence conditions in Equation (13) appear to yield reconstructions of practical relevance, as the study results below show.

Prior to physical-phantom and human studies, we conducted a Monte-Carlo-simulation study in which full data of ~200 million total counts were generated from the digital Jaszczak phantom by using the GATE simulation package for the full-scan configuration 12F (FIG. 1A). From the full data, we also extracted sparse data (thus simulating the sparse configuration 12S) and carried out reconstructions for the sparse-scan configuration. Without loss of generality, the simulation study includes only truth events. Images are reconstructed on a 3D array of 70×70×41 identical cubic voxels of size 4 mm. Digital phantom $u_{true}$ consists of cold- and hot-rod sections each of which contains six types of cylindrical-shaped rods of diameters 4.8, 6.4, 7.9, 9.5, 11.1, and 12.7 mm. Although GATE data contain only true coincidence events, they are inconsistent with the model data in Equation (1) due to noise and other physical factors included by GATE, but not in the data model. Using GATE data and knowledge of truth image $u_{true}$, we characterize how optimization-based reconstruction responds to data inconsistency prior to its application to real data in which knowledge of the truth image is unavailable.

In a first aspect of the Monte-Carlo simulations, the TV-constraint parameter $t_0$ was determined. More particularly, in the study, given the convergence conditions in Equation (13), all of the program parameters are determined, except for TV-constraint parameter $t_0$, which is determined by use of the root-mean-square error (RMSE):

$$RMSE = \frac{1}{\sqrt{N}} \|u_{true} - \hat{u}^*\|_2 \qquad (14)$$

between truth image $u_{true}$ and convergent reconstruction $\hat{u}^*$. For each of a set of $t_0$ values, we solve program DKL-fTV in Equation (4) to obtain convergent reconstruction $\hat{u}^*$ from full data and calculate the RMSE. Repeating the reconstruction and calculation for all values of $t_0$, we obtain an RMSE of $t_0$.

Figure 4A:
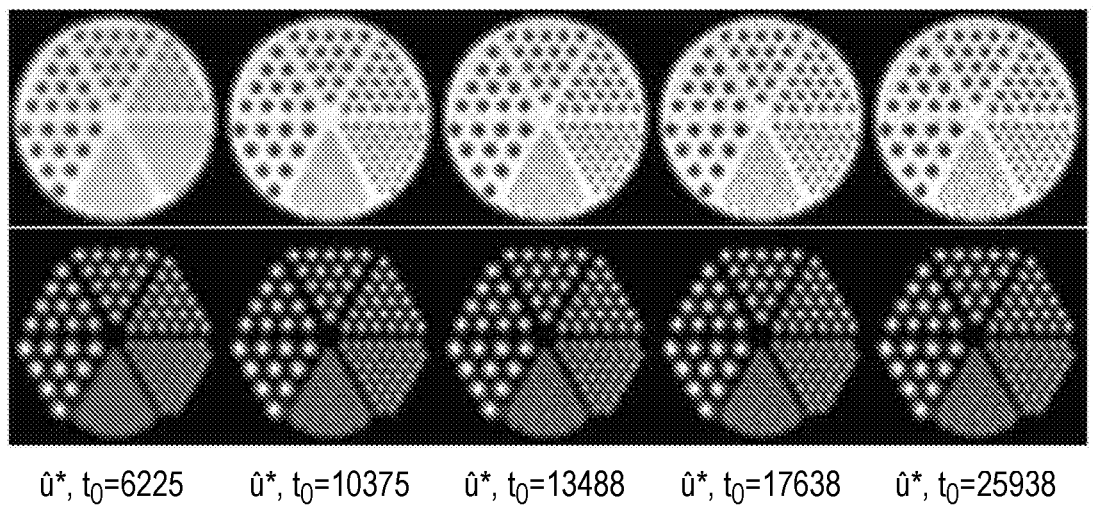
Figure 4B:
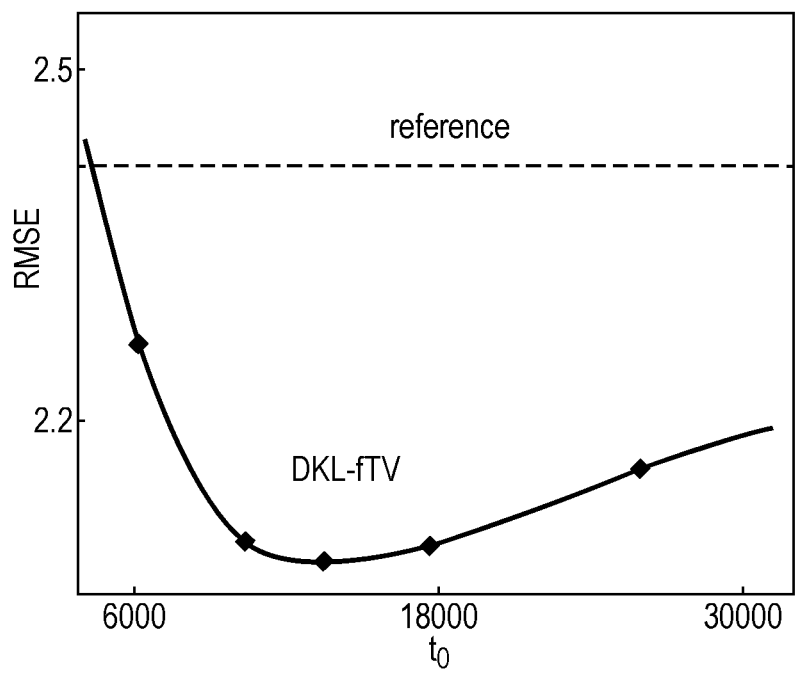

FIG. 4A shows convergent reconstructions $\hat{u}^*$ within transverse slices containing cold (row 1) and hot (row 2) rods in the Jaszczak phantom obtained from full data with program DKL-fTV for different $t_0$ values. The plot of FIG. 4B shows metrics RMSE calculated from $\hat{u}^*$ (solid) and the reference reconstruction (dashed), as functions of $t_0$. Based upon the RMSE result, we selected $t_0=13488$, which yields a minimum RMSE, for obtaining reconstruction results in subsequent sections. The RMSE metric was used for selecting $t_0$ in the study because knowledge of truth image $u_{true}$ is available.

Figure 5:
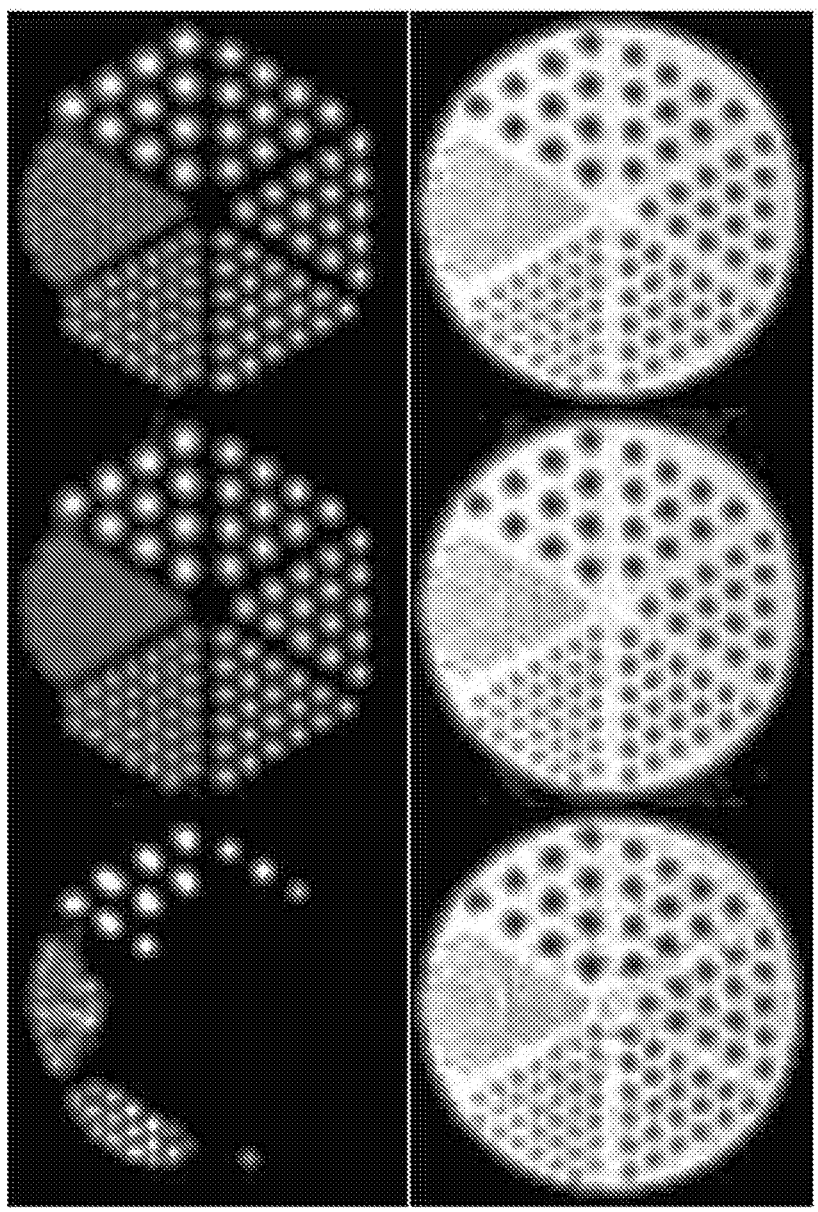

Next, the different optimization programs were compared via Monte-Carlo simulations. Using the selected $t_0$, we obtained reconstructions from full data by solving programs DKL-fTV, DL2-fTV, and DL1-fTV in Equations (4)-(6), and these reconstructions are shown in FIG. 5. More particularly, FIG. 5 shows convergent reconstructions $\hat{u}^*$ within transverse slices containing cold (row 1) and hot (row 2) rods in the Jaszczak phantom obtained from full data with programs DKL-fTV, DL2-fTV, and DL1-fTV in Equations (4)-(6), respectively. Display windows for FIG. 5 are: [0, 40000] (row 1) and [0, 15000] (row 2). It can be observed that all of the convergent reconstructions $\hat{u}^*$ for the cold-rod section appear visually comparable, only with slightly different noise textures, while program DKL-fTV yields a reconstruction of the hot-rod section with spatial resolution slightly superior to those obtained with programs DL2-fTV and DL1-fTV. However, the DL1-fTV reconstruction of the hot-rod section appears to contain prominent zero-valued artifacts. Indeed, the DL1-fTV reconstructions from data of the IEC phantom and human subject reported later herein also shows significant artifacts (see FIGS. 11 and 18).

In an effort to elicit the artifact source, we define:

$$g'_m = g_m - g_s - g_r \text{ and } g' = \mathcal{H}\hat{u}^* \qquad (15)$$

where $g'_m$ denotes the measured data with scatter/random corrected for, and $g'$ the model data estimated from the convergent reconstruction $\hat{u}^*$, also with scatter/random corrected for. In particular, we use $g'_{KL}$, $g'_{\ell_2}$, and $g'_{\ell_1}$ to specify explicitly the model data estimated, respectively, by use of programs DKL-fTV, DL2-fTV, and DL1-fTV.

Figure 6:
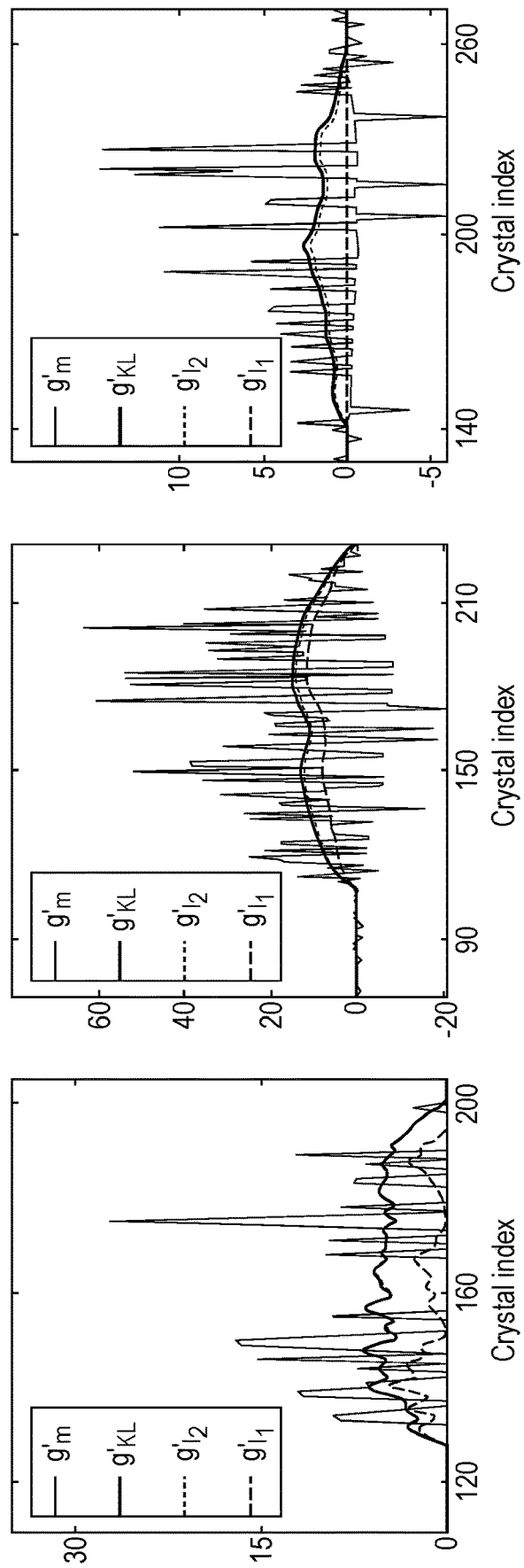

With reference to FIGS. 6A, 6B, and 6C, profiles are shown of measured data $g'_m$ (thin solid), and model data $g'_{KL}$ (thick solid), $g'_{\ell_2}$ (dotted), and $g'_{\ell_1}$ (dashed) obtained with programs DKL-fTV, DL2-fTV, and DL1-fTV for the Jaszczak phantom (FIG. 6A), the IEC phantom (FIG. 6B), and a human subject (FIG. 6C). The profile results suggest that the minimization of data $\ell_1$-norm in program DL1-fTV yields the estimated model data biased toward zero due to the prevalence of zero or small-valued measurements, thus producing artifacts observed in the DL1-fTV-based reconstruction of the hot-rod section in FIG. 5. It is possible that artifacts in DL1-fTV reconstructions may be different when program parameters different than those used here.

The foregoing results indicate that for the subject data sets the program DKL-fTV produces reconstructions of reasonable visual textures for both cold- and hot-rod sections. Thus, optimization program DKL-fTV was chosen as the optimization program for further investigations. (As can be seen from the example in FIG. 18, the DKL-fTV reconstructions tended to have better delineated boundaries than the DL2-fTV reconstructions, while DL1-fTV yielded zero-valued reconstructions.) For completeness, visualization of converged patient data reconstructions (not shown) was conducted at different values of $t_0$ for each optimization program. The results of patient data reconstructions at different values of $t_0$ showed the same trends at all values of $t_0$ considered. Thus, in the following, the DKL-fTV program was used except where otherwise noted.

Figure 7:
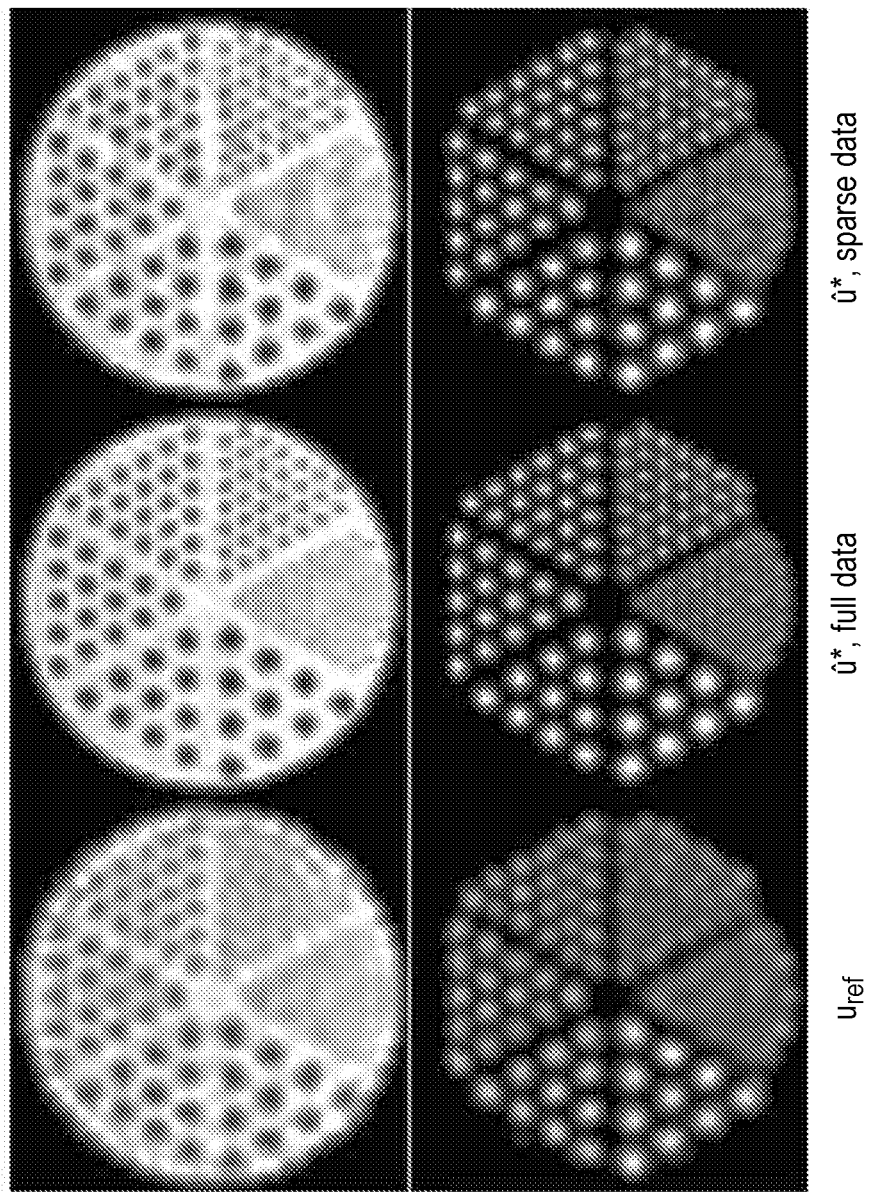

FIG. 7 shows reference reconstructions (left column labeled $u_{ref}$), and convergent reconstructions $\hat{u}^*$ within transverse slices containing cold rods (row 1) and hot rods (row 2) in the Jaszczak phantom obtained from full data (middle column) and sparse data (right column). The optimization program DKL-fTV was used for these reconstructions. In FIG. 7, the display windows are: [0, 40000] (row 1) and [0, 15000] (row 2). In FIG. 7, the convergent reconstructions $\hat{u}^*$ were obtained from both full and sparse data by use of the CP algorithm to solve DKL-fTV with $t_0=13488$. The results indicate that, in general, reconstructions from full data appear visually to possess better spatial resolution and lower noise level than do those from sparse data, and that reconstructions obtained with program DKL-fTV seem to reveal enhanced spatial and contrast resolution in which hot/cold rods of size 6.4 mm appear to remain resolved.

Figure 8:
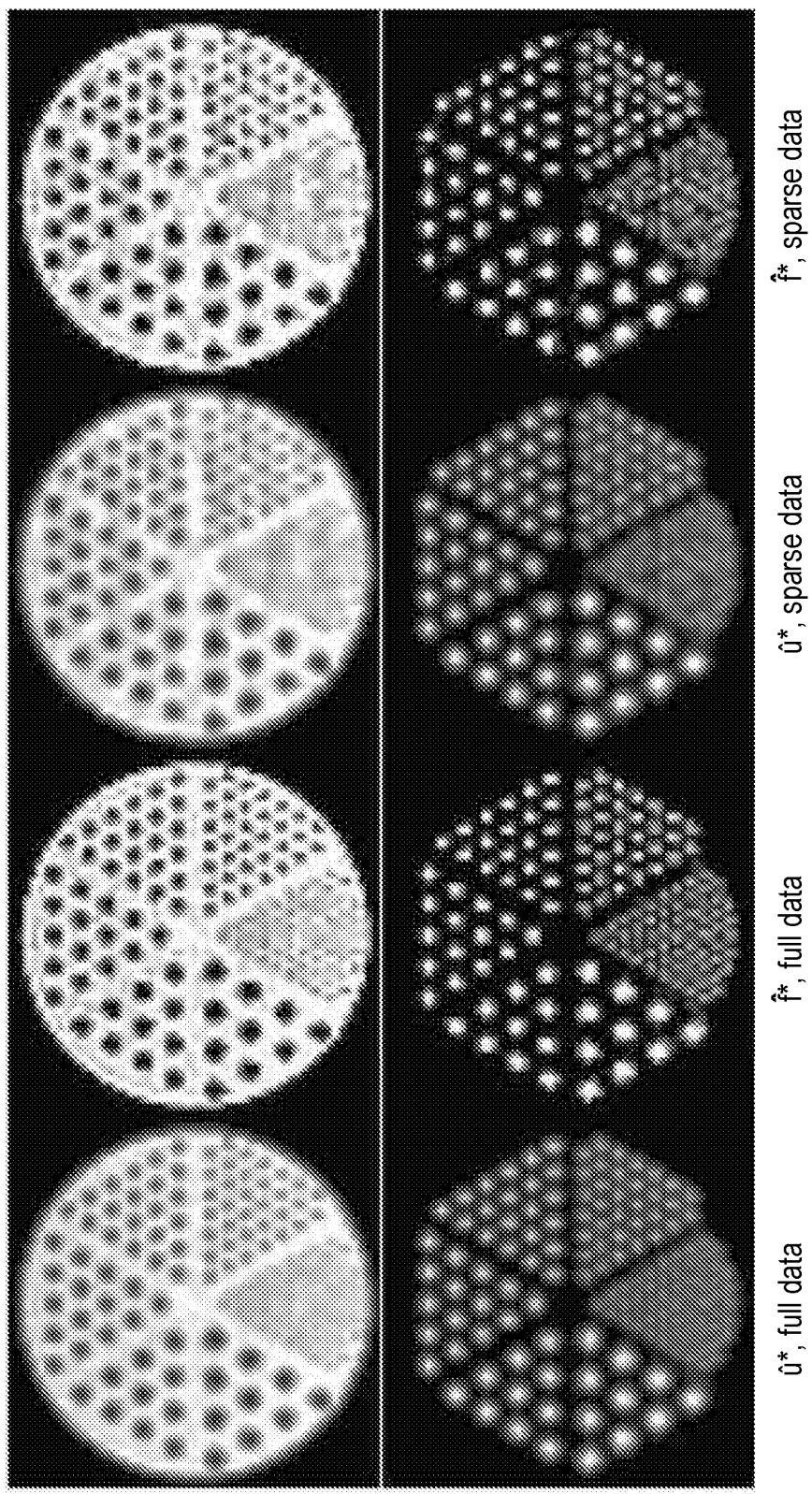

As shown in the pseudo-code (Algorithm) for the CP algorithm, latent image f defined in Equation (3) can also be reconstructed. FIG. 8 shows convergent reconstructions $\hat{u}^*$ and $\hat{f}^*$ within transverse slices containing cold rods (row 1) and hot rods (row 2) in the Jaszczak phantom obtained from full data (leftmost two columns) and sparse data (rightmost two columns), again using optimization program DKL-fTV. Display windows in FIG. 8 are: [0, 40000] (row 1) and [0, 15000] (row 2). As shown in FIG. 8, it can be observed that $\hat{f}^*$ tends to have noisier textures than $\hat{u}^*$.

Reconstruction as a function of iterations is next considered.

Figure 9A:
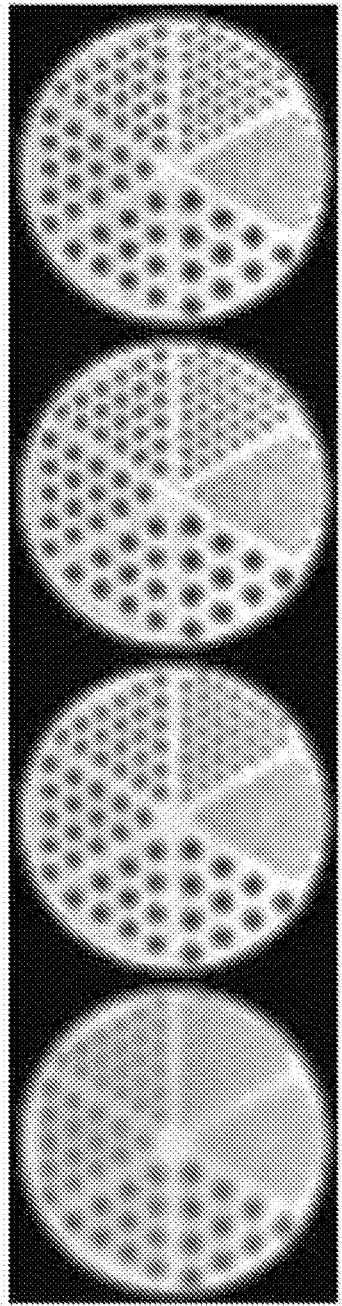
Figure 9B:
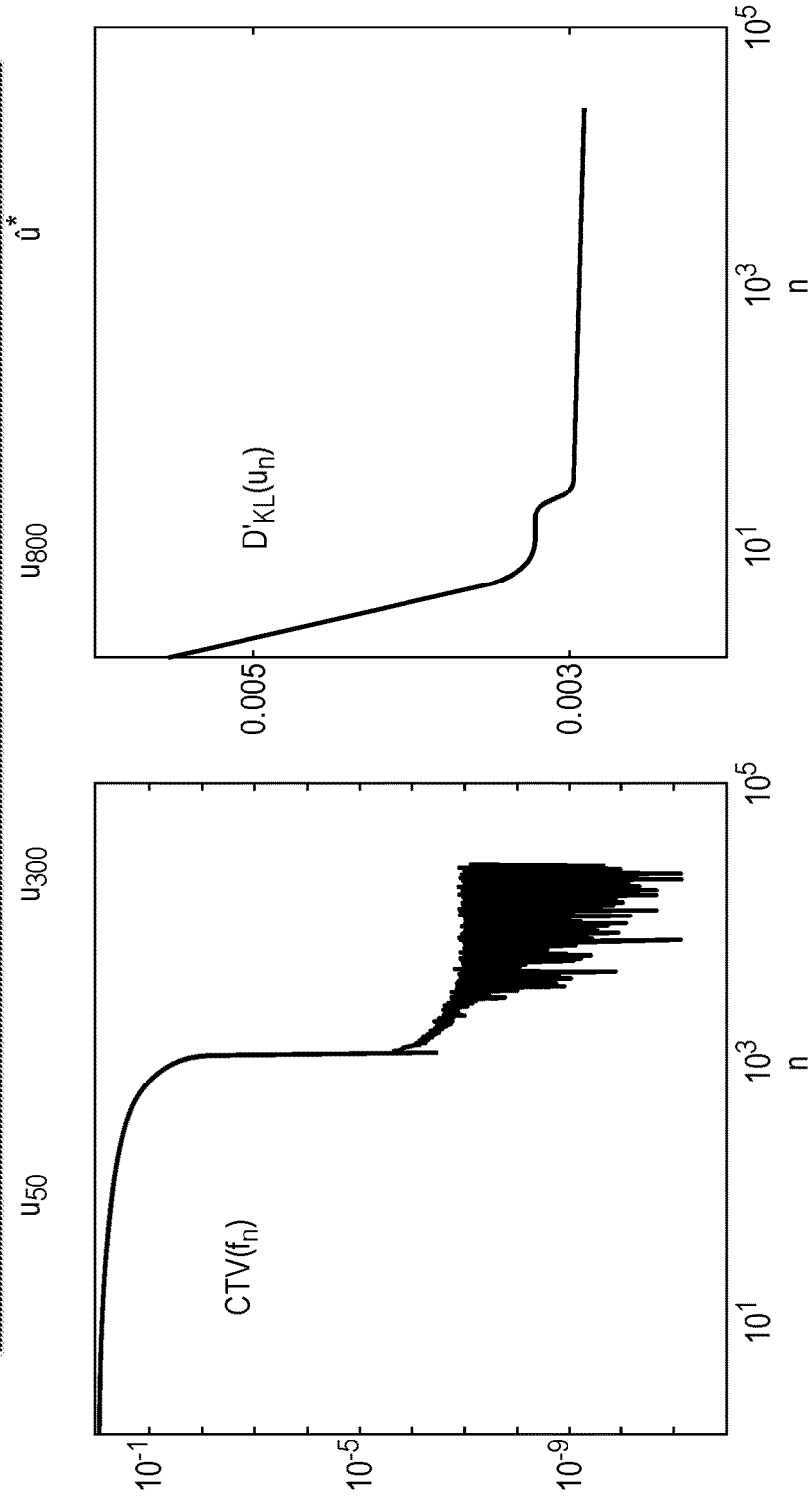

The reconstructions above were obtained when the convergence conditions in (Equation (13)) were satisfied. To inspect how reconstructions evolve as a function of iterations, FIG. 9A shows reconstructions $u_n$ at iteration n=50, 300, and 800 within a transverse image containing cold rods in the Jaszczak phantom from full data with program DKL-fTV, along with convergent reconstruction û* (obtained at iteration 71160). Display windows in FIG. 9A are: [0, 40000]. FIG. 9B shows plots displaying convergence metrics CTV($f_n$) and D'$_{KL}$($u_n$) as functions of iterations n. Similar reconstructions and plots were obtained also for the sparse-data study, but are not shown here. These results reveal that the reconstruction at, e.g., about iterations 300 is visually similar to the convergent reconstruction.

In a next set of experiments, physical phantom data studies were performed using an IEC phantom. We collected full data of: 100 million total counts from the phantom by using a full-scan configuration in a digital prototype PET/CT system. From the full data, we extracted sparse data to mimic data collected with the sparse-scan configuration. The IEC phantom is composed of 6 fillable spheres of diameters 10, 13, 17, 22, 28, and 37 mm, respectively, in which the two largest spheres have zero activity, while the other four spheres are filled with positron-emitter activity at a concentration level four times the background-activity level. Scatter and random events were measured, and used as known components in the study. Images were reconstructed on a 3D array of 100×100×41 identical cubic voxels of size 4 mm.

A first task was determination of the image-constraint parameter $t_0$. In the study, given the practical convergence conditions in Equation (13), all program parameters except the image-constraint parameter $t_0$ were determined as described. Percent contrasts of hot and cold spheres and percent background variability, described in the Appendix, are standard metrics designed for evaluation of reconstruction quality of the IEC-phantom. In this study, full knowledge of the truth image is unknown. Therefore, combining the metrics, we form in the Appendix a single quality metric, referred to as the QNR, for determination of $t_0$. For a set of $t_0$ values, convergent reconstructions from full data of the IEC phantom were obtained by use of the CP algorithm to solve program DKL-fTV in Equation (4).

Figure 10A:
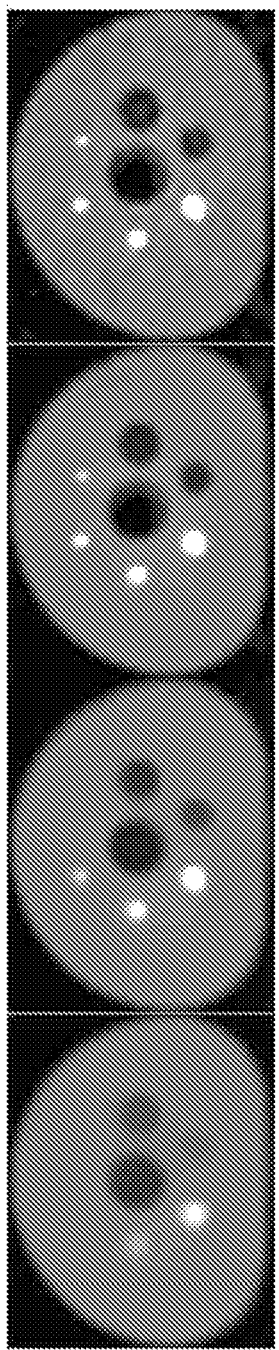
Figure 10B:
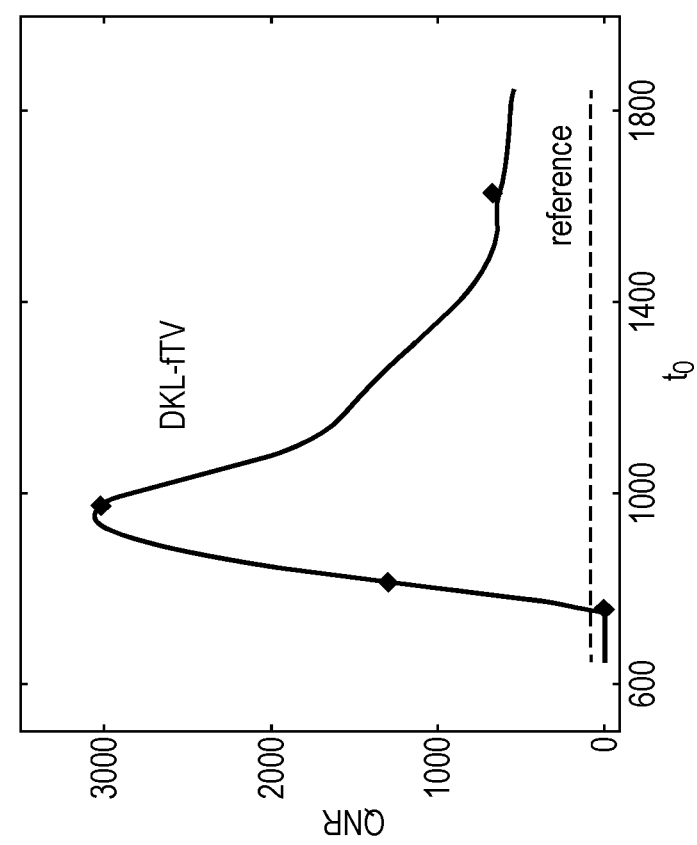

The QNRs calculated from the reconstructions are plotted in FIG. 10B, along with the reconstructions (FIG. 10A) with the QNRs of these reconstructions highlighted by black diamonds in the plots of FIG. 10B. More particularly, FIG. 10A shows convergent reconstructions û* within the central transverse slice of the IEC phantom obtained from full data with program DKL-fTV for different $t_0$ values. FIG. 10B plots metrics QNR calculated from û* (solid) and the reference reconstruction (dashed), as functions of $t_0$. Based upon the QNR result, we selected $t_0$=977, which yields a maximum QNR in the plot, for reconstructions from full and sparse data of the IEC phantom below.

Figure 11:
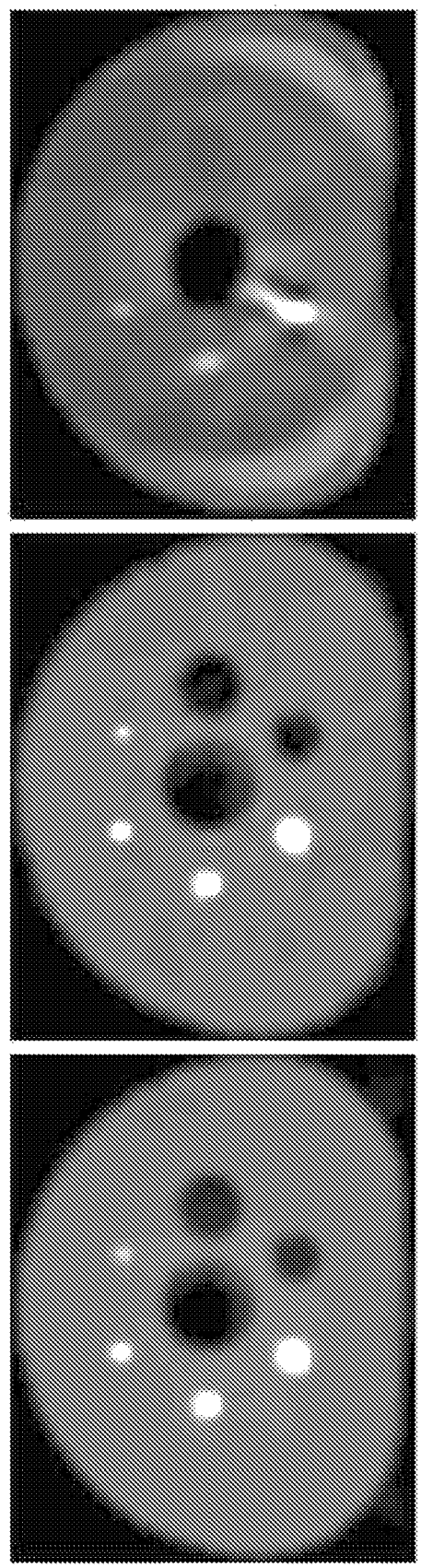

Reconstructions based upon different optimization programs was also investigated. FIG. 11 shows convergent reconstructions û* within the central transverse slice of the IEC phantom obtained from full data with programs DKL-fTV, DL2-fTV, and DL1-fTV, respectively (see Equations (4)-(6)). The display windows in FIG. 11 are: [0, 16000]. Again, it is observed that convergent reconstructions obtained with programs DKL-fTV and DL2-fTV appear visually comparable, while the DL2-fTV reconstruction has slightly noisier textures than the DKL-fTV reconstruction. By contrast, the program DL1-fTV yields reconstructions with prominent cupping artifacts. Similar to the results obtained in the Jaszczak-phantom study, the data-$\ell_1$-norm minimization yields the estimated model data of the IEC phantom biased toward zero (cf. FIG. 6b), and such a data-estimate bias is believed to give rise to the artifacts observed in the DL1-fTV-based reconstruction of the IEC phantom in FIG. 11. Again, artifacts in the DL1-fTV reconstruction may vary with program parameters different than those used in the work.

Figure 12:
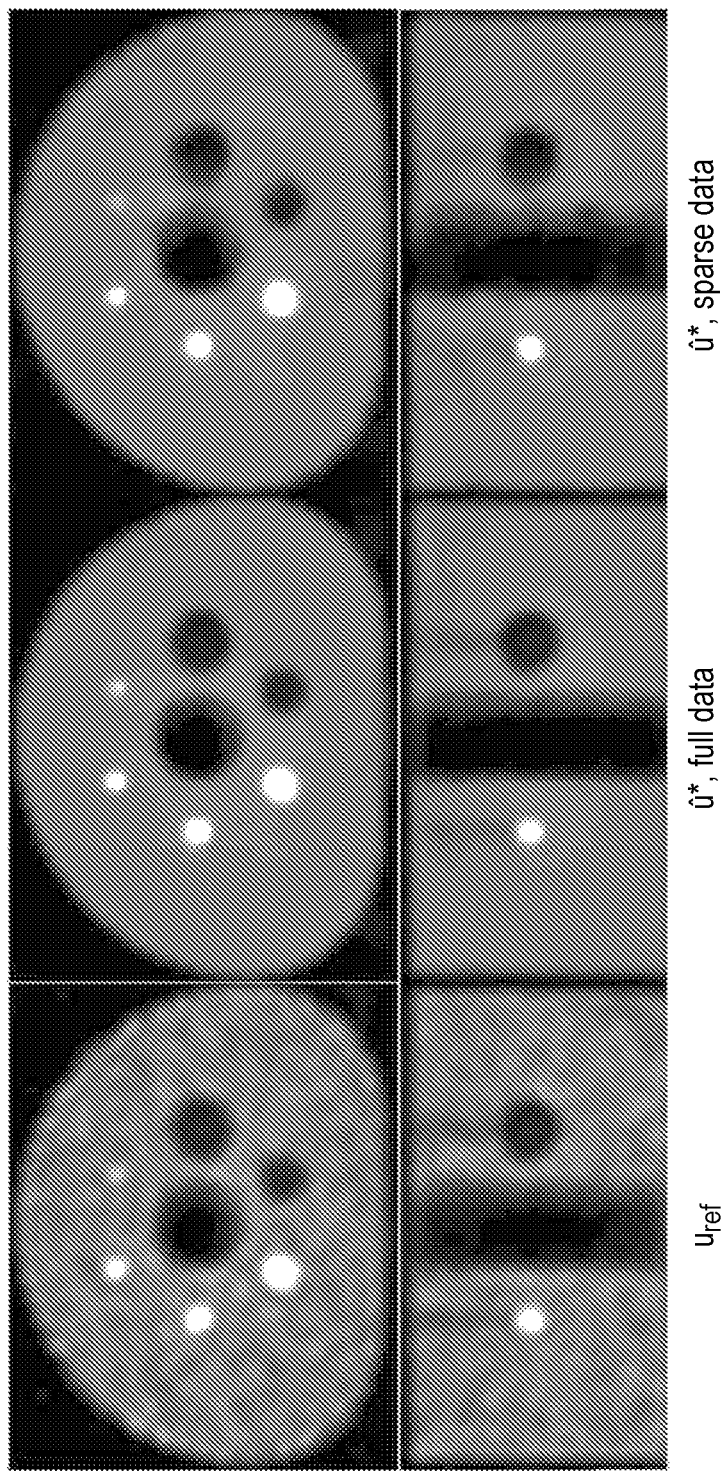

In view of the foregoing, reconstructions using optimization program DKL-fTV were chosen for further investigation. FIG. 12 shows reference reconstructions (left column), and convergent reconstructions û*, within the central transverse slice (row 1) and central coronal slice (row 2) of the IEC phantom, obtained from full data (middle column) and sparse data (right column) with program DKL-fTV. The display windows in FIG. 12 are: [0, 16000]. As expected, the reconstruction from full data appears to have a level of spatial and contrast resolution slightly higher than the reconstruction from sparse data, while both convergent reconstructions have a relatively low level of background noise in which the hot spot of the smallest size (i.e., diameter of 10 mm) remains visible.

Figure 13:
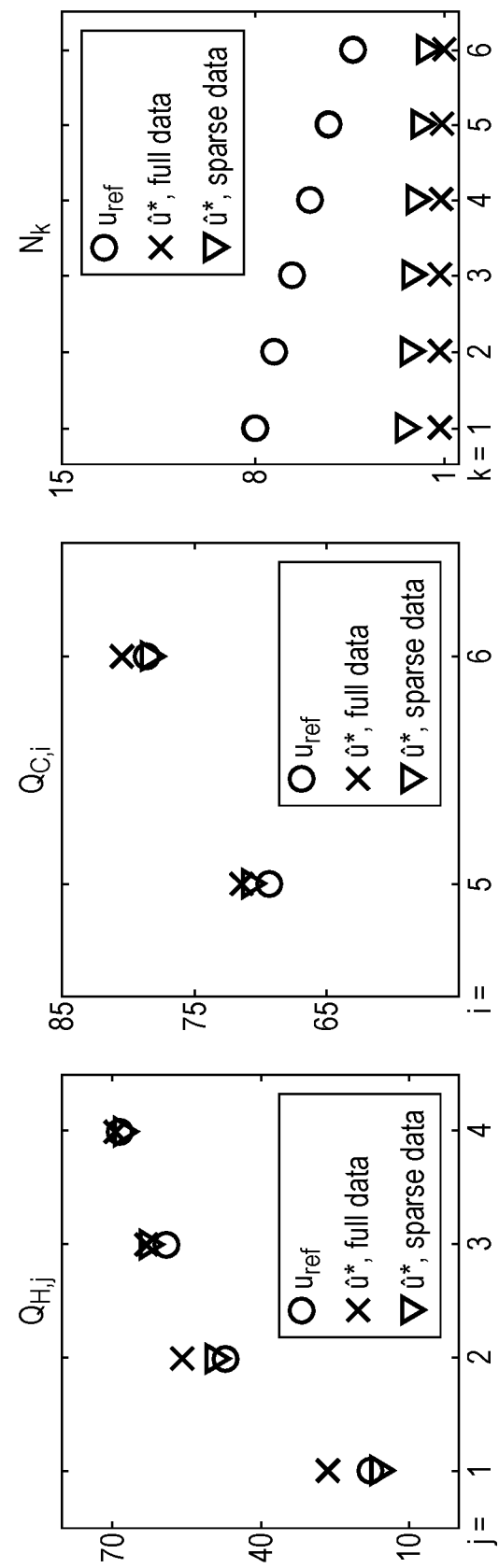

We computed from the reconstructions quantitative metrics described in the Appendix, and display them in FIG. 13, which plots: percent contrast $Q_{H,j}$ of hot spheres (left plot), where j=1, 2, 3, and 4; percent contrast $Q_{C,i}$ of cold spheres (middle plot), where i=5 and 6; and percent background variability $N_k$ (right plot), where k=1, 2, 3, 4, 5, and 6, respectively, calculated based upon reference reconstruction ($u_{ref}$) and convergent reconstructions û* from full and sparse data of the IEC phantom shown in FIG. 12. These results suggest that convergent reconstructions from sparse data are slightly inferior to those from full data, as expected, and that they appear to be largely comparable to, or better than, the reference reconstructions from full data.

Figure 14:
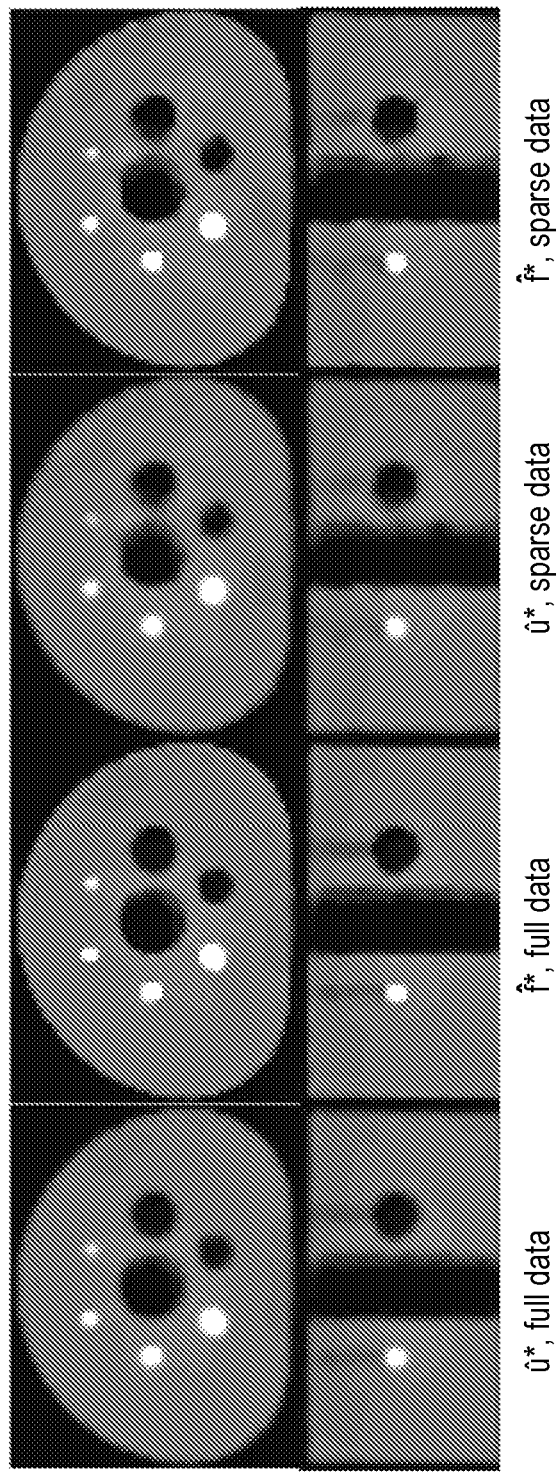

FIG. 14 displays convergent reconstructions û* and f̂* within the central transverse slice (row 1) and the central coronal slice (row 2) of the IEC phantom obtained from full data (two leftmost columns) and sparse data (two rightmost columns) with optimization program DKL-fTV. Display window: [0, 16000]. Again, comparing the convergent reconstructions û* and f̂* of desired and latent images u and f, we observe that the latter is slightly noisier than the former.

Figure 15:
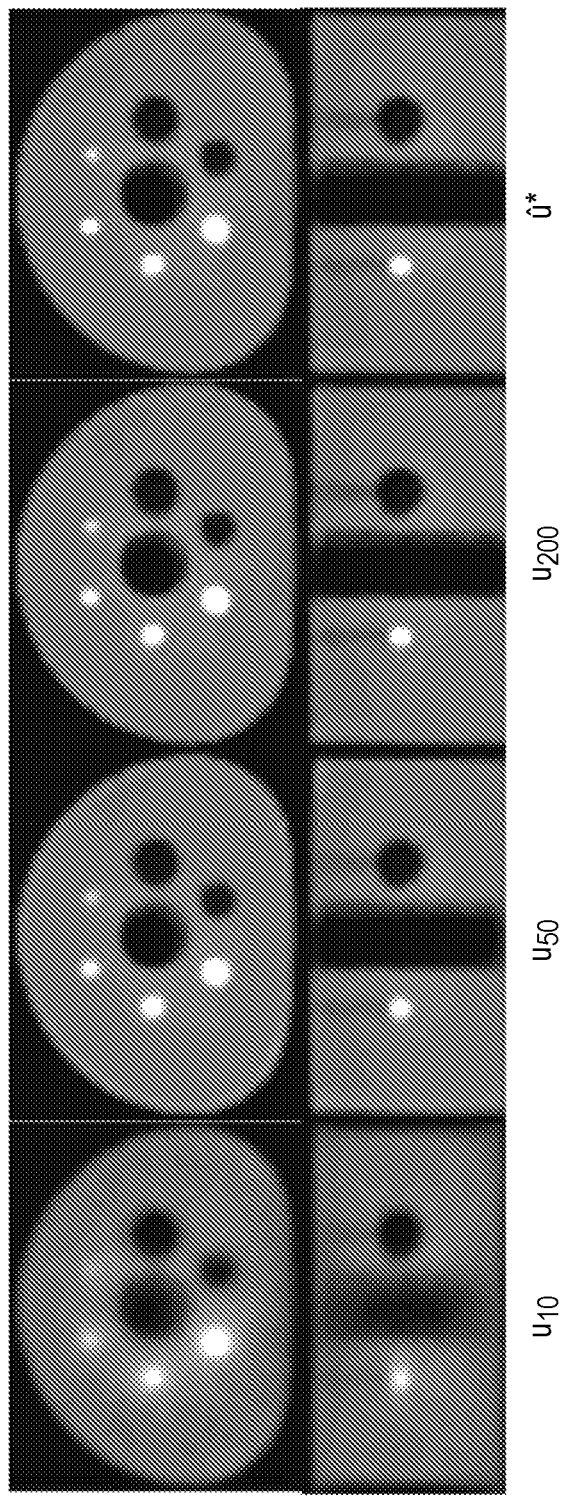

Reconstruction as a function of iterations was next investigated. Convergent reconstructions û* of the IEC phantom were obtained again when the convergence conditions in Equation (13) are satisfied. FIG. 15 shows reconstructions $u_n$ at iteration n=10, 50, and 200, along with the convergent reconstruction (obtained at iteration 2701), within the central transverse slice (row 1) and central coronal slice (row 2) of the IEC phantom obtained from full data with program DKL-fTV. In FIG. 15 the display windows are: [0, 16000]. It is observed that the reconstruction at, e.g., about iteration 200 visually resembles convergent reconstruction û*. Similar observations can be made for reconstructions obtained from sparse data (not shown).

Figure 16:
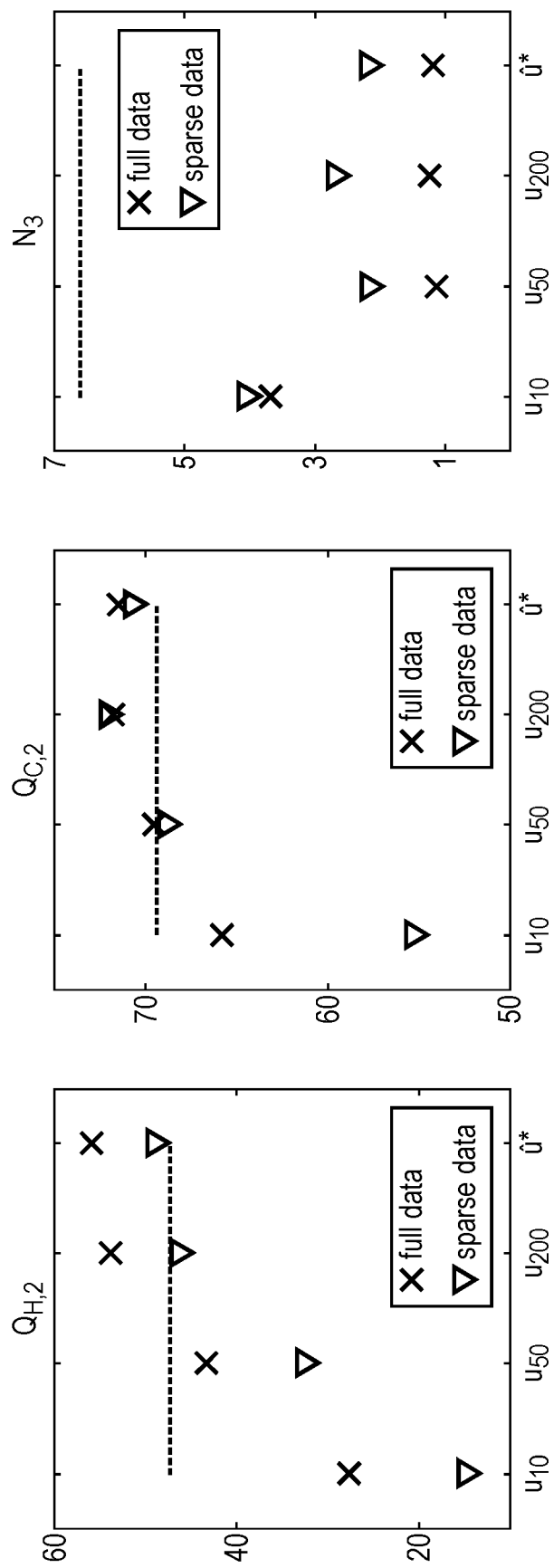

FIG. 16 shows calculated quality metrics described in the Appendix from full- and sparse-data reconstructions at different iterations shown in of FIG. 15. FIG. 16 plots: $Q_{H,2}$ of the hot sphere 2 with a diameter of 13 mm (left plot); $Q_{C,5}$ of the cold sphere 5 with a diameter of 28 mm (middle plot); and $N_3$ within the ROIs of size 17 mm of sphere 3 (right plot). The results plotted in FIG. 16 confirm that reconstructions at about iteration 200 resemble their corresponding convergent reconstructions.

In addition to the phantom studies reported above with reference to FIGS. 2-16, a human data study was also performed. In the human-data study, full data were acquired from the subject by use of the full-scan configuration (see FIG. 1A) in a digital prototype PET/CT system at a single patient-bed position. To increase the longitudinal coverage of the human subject, five full scans were performed at five bed positions along the central axis of the system with a separation of 70 mm between the centers of two consecutive bed positions. The five sets of full data acquired contain approximately 23.9, 25.0, 26.7, 24.3, and 22.1 million total counts. A sparse data set was extracted from each one of the five sets of full data, thus yielding a corresponding five sparse data sets. Scatter and random measurements were included in the study. The human image was reconstructed on a 3D array consisting of N=144×144×41 identical cubic voxels of size 4 mm.

Determination of the image-constraint parameter $t_0$ was first considered. Again, given the practical convergence conditions in Equation (13), all of the program parameters except image-constraint parameter $t_0$ were determined as previously described. Unlike the phantom studies, in which quantitative metrics were used for selecting $t_0$, for the human study $t_0$ was selected based upon qualitative visual inspection.

Figure 17:
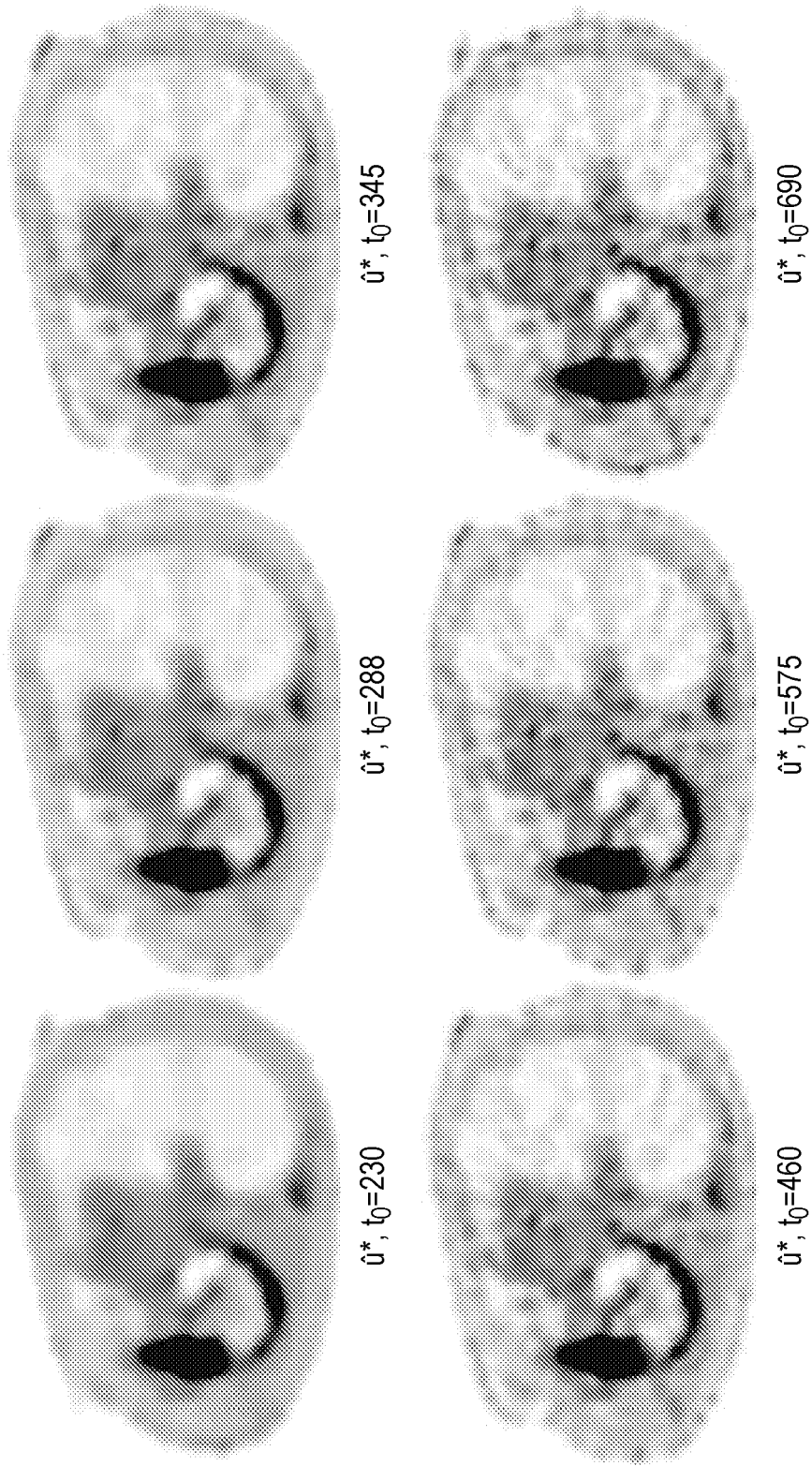

FIG. 17 shows negative convergent reconstructions $\hat{u}^*$ within a transverse slice of the human subject obtained from full data at bed position 3 with program DKL-fTV for different $t_0$ values. In FIG. 17, the display windows are: [−1600, 0]. FIG. 17 shows convergent reconstructions obtained with $t_0$=230, 287, 345, 460, 575, and 690, respectively. As expected, high $t_0$ values yield reconstructions with noisy texture while revealing some additional structural details; whereas, low $t_0$ values lead to reconstructions with smoothed texture but which are missing some structural details. Based upon visual inspection of the reconstructions, $t_0$=460 was selected as it appears to yield reconstructions with a reasonable balance between structural details and image-noise texture. Using the same method, $t_0$ values were determined for reconstructions from other full- and sparse-data sets.

Figure 18:
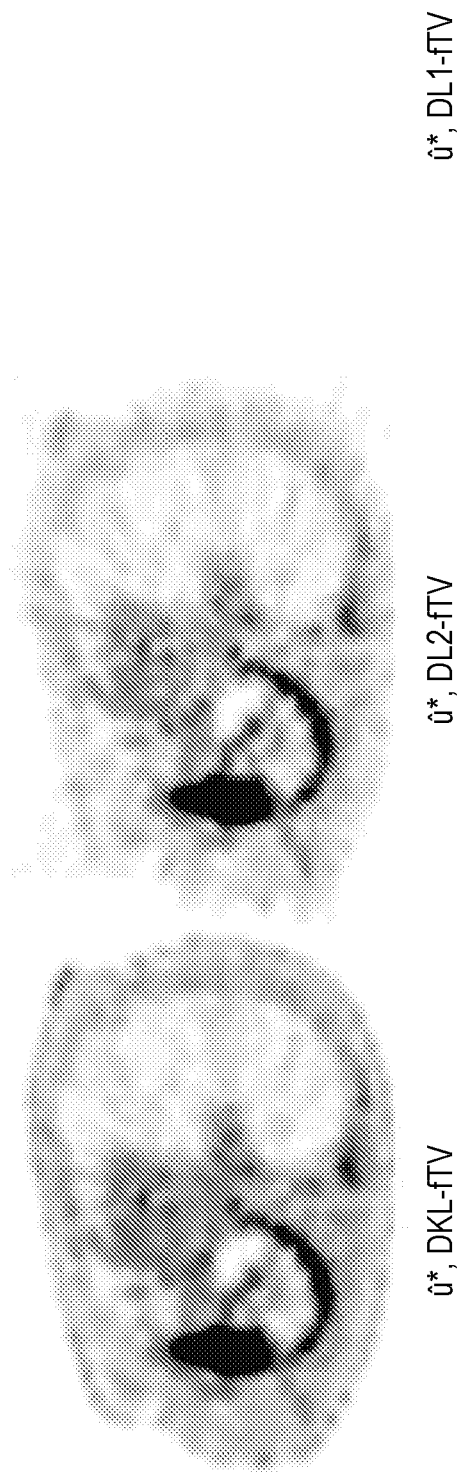

With reference to FIG. 18, reconstructions using different optimization programs were investigated. FIG. 18 shows negative convergent reconstructions $\hat{u}^*$ within a transverse slice of the human subject obtained from full data at bed position 3 with programs DKL-fTV (left image), DL2-fTV (middle image), and DL1-fTV (right image). Note that the right image obtained using optimization program DL1-fTV yields a zero-valued reconstruction. In FIG. 18, the display windows are: [−1600, 0]. In these reconstructions, for full data collected at a single bed position, we selected $t_0$ as described with reference to FIG. 17, and then reconstructed human images by solving the three programs of Equations (4)-(6). FIG. 18 shows the reconstructions from full data collected at bed position 3. The reconstruction obtained with program DKL-fTV appears to possess better delineated boundaries, more structural details, and lower texture noise than do that obtained with program DL2-fTV. However, program DL1-fTV yields a convergent reconstruction with strong artifacts, namely numerically zero values, as depicted in the "blank" right image of FIG. 18. Again, the estimated model data become negatively biased as a result of the data-$\ell_1$-norm minimization and scatter correction. Consequently, zero-valued estimated model data revealed in FIG. 6c and, the zero-valued $\hat{u}^*$ (or, equivalently, zero-valued $\hat{f}^*$) shown in FIG. 18, were obtained with the positivity constraint. When different program parameters such as $t_0$ are used, program DL1-fTV may yield reconstructions different than a zero-valued image. Although not shown, similar results were obtained for reconstructions from full and sparse data collected at this and other bed positions.

In view of the foregoing, the optimization program DKL-fTV was selected for use in further investigations. For a single bed position, using $t_0$ selected as described with reference to FIG. 17, we reconstructed images from full data collected by using the CP algorithm to solve program DKL-fTV. Repeating this for all of the five bed positions, we obtained five convergent reconstructions, and then summed them up to form a final-convergent reconstruction with an extended longitudinal coverage. Following the same procedure, we also obtained the final-convergent reconstruction of the human subject from the five sets of sparse data.

Figure 19:
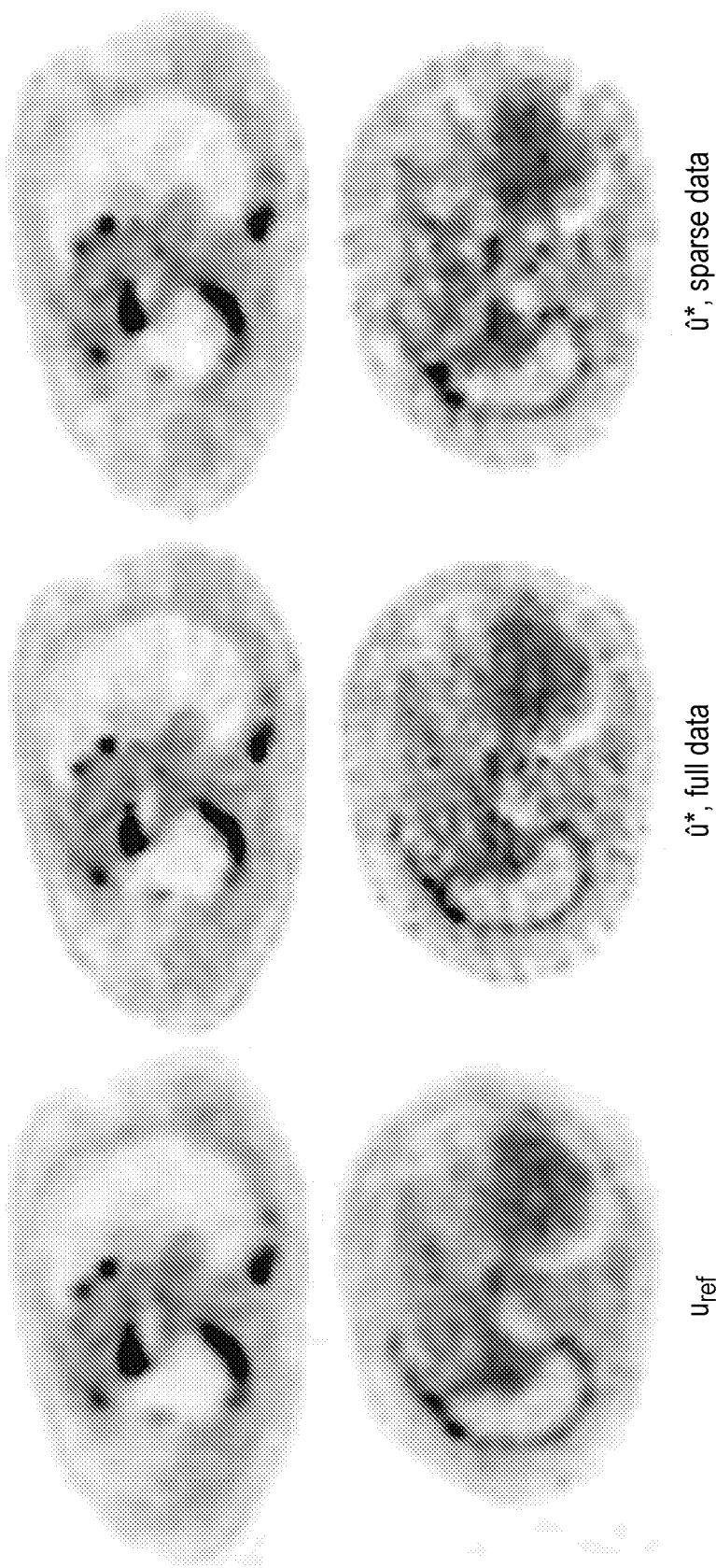
Figure 20:
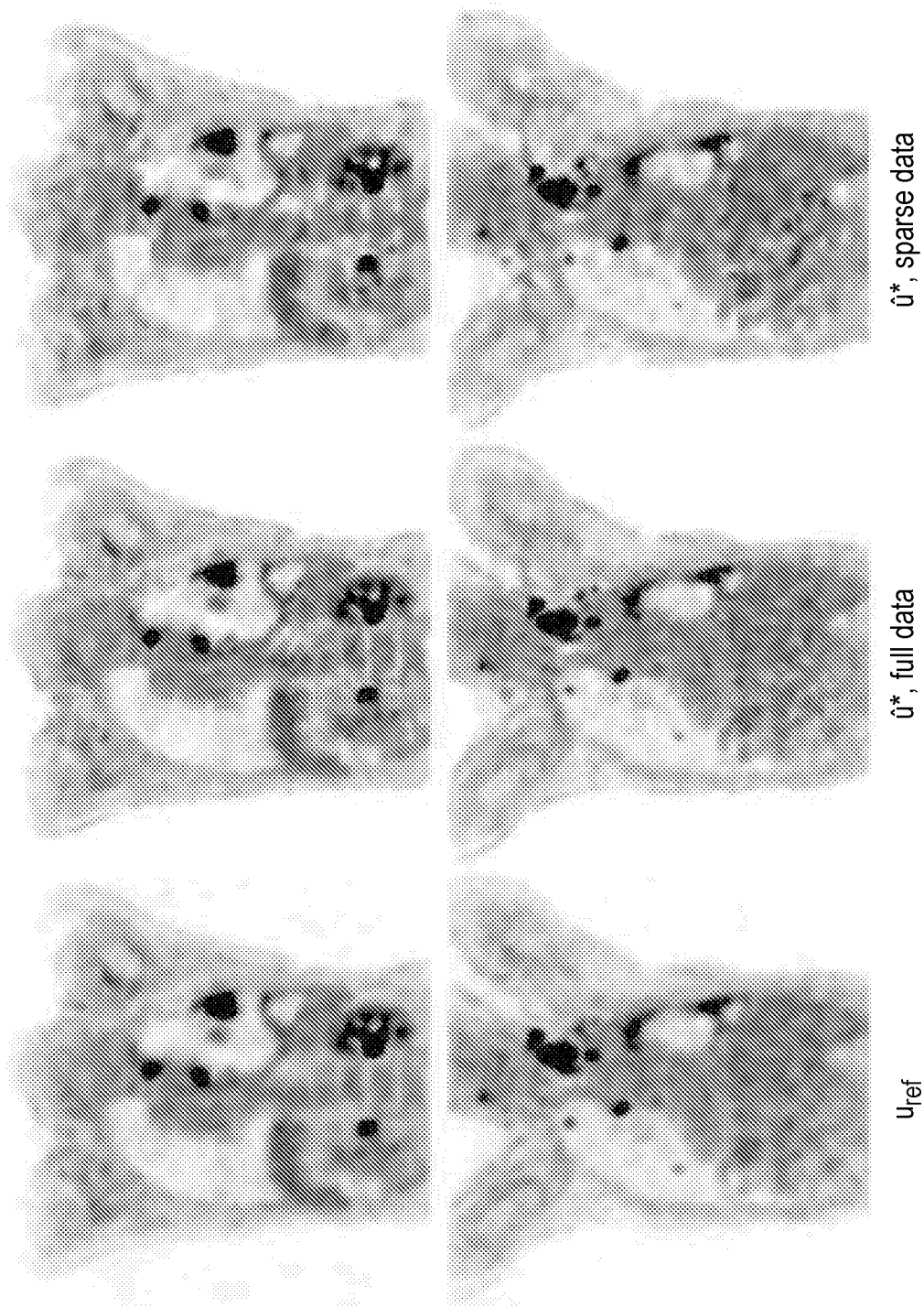
Figure 21:
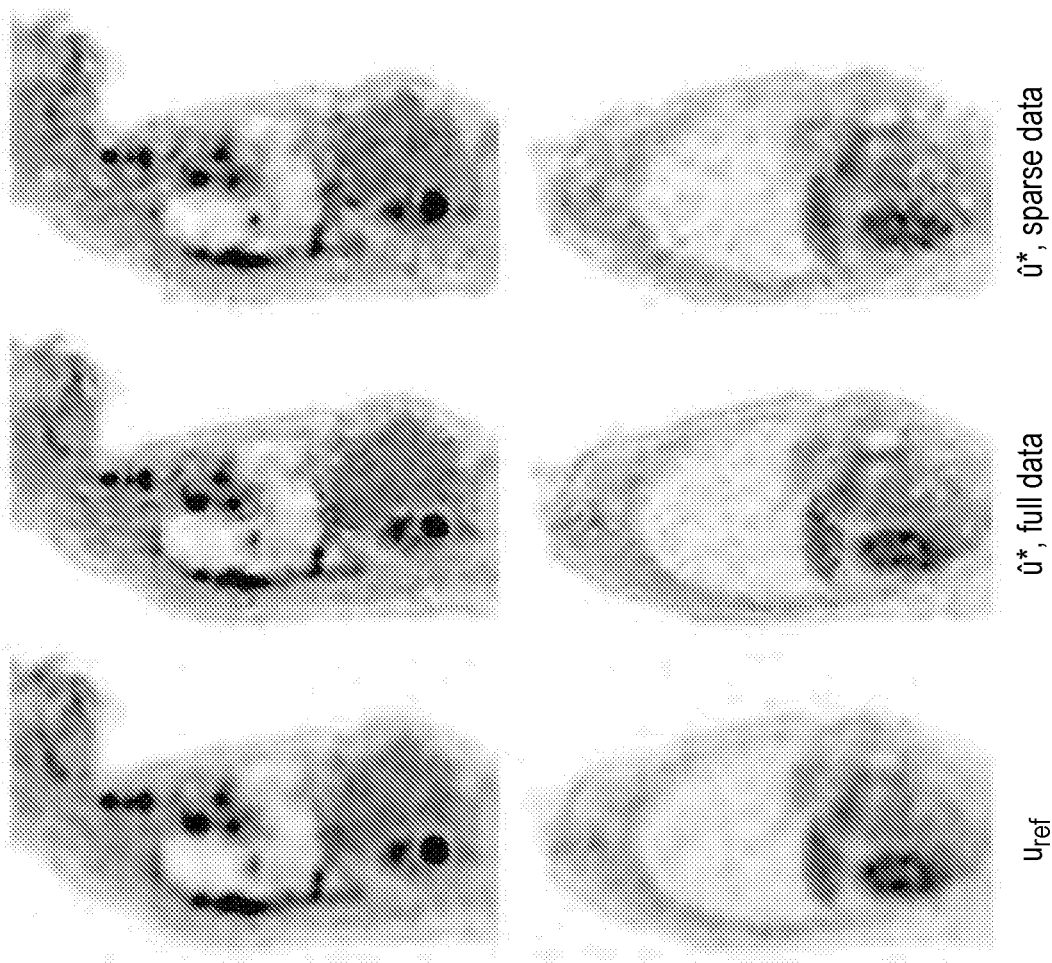

With reference to FIGS. 19-21, the final-convergent reconstructions are displayed within transverse, coronal, and sagittal slices of the human subject.

FIG. 19 shows negative reference reconstructions (left column), and negative final-convergent reconstructions $\hat{u}^*$, within two transverse slices (rows 1 and 2) of the human subject obtained from full data (middle column) and sparse data (right column) with program DKL-fTV. In FIG. 19 the display windows are [−1600, 0].

FIG. 20 shows negative reference reconstructions (left column), and negative final-convergent reconstructions $\hat{u}^*$, within two coronal slices (rows 1 and 2) of the human subject obtained from full data (middle column) and sparse data (right column) with program DKL-fTV. In FIG. 20 the display windows are [−1600, 0].

FIG. 21 shows negative reference reconstructions (left column), and negative final-convergent reconstructions $\hat{u}^*$, within two sagittal slices (rows 1 and 2) of the human subject obtained from full data (middle column) and sparse data (right column) with program DKL-fTV. In FIG. 21 the display windows are [−1600, 0].

With reference to FIGS. 19-21, it is observed that program DKL-fTV appears to yield reconstructions from full data with well-delineated boundaries and suppressed noise in the background region. Similar observation can be drawn for reconstructions from sparse data as well, although reconstructions from sparse data are visually somewhat noisier than those from full data, as expected.

Figure 22:
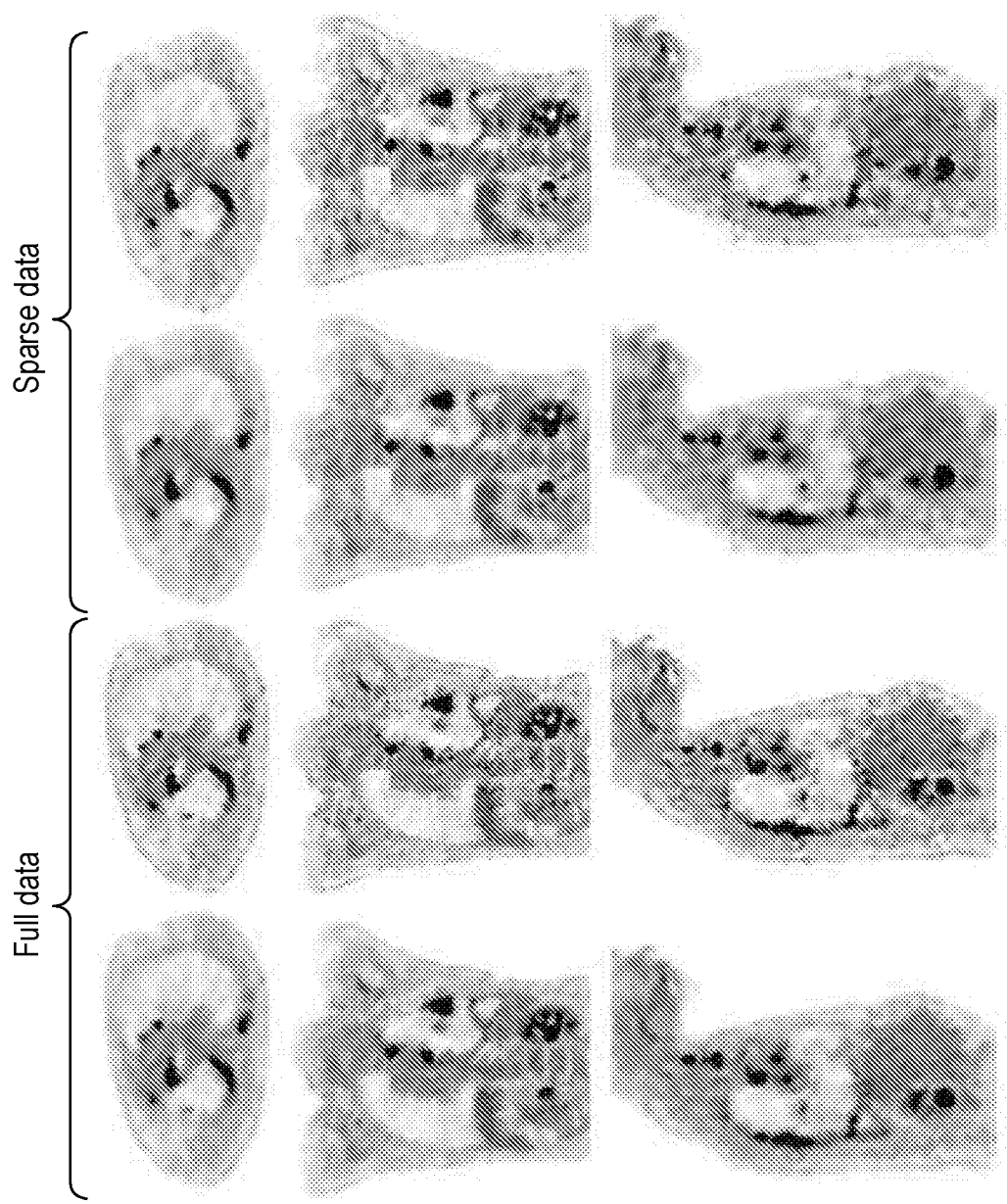

FIG. 22 shows negative final-convergent reconstructions $\hat{u}^*$ and $\hat{f}^*$ of desired and latent images u and f within a transverse slice (row 1), a coronal slice (row 2), and a sagittal slice (row 3) of the human subject obtained from full data (columns 1 & 2) and sparse data (columns 3 & 4) with program DKL-fTV. Display windows for the images in FIG. 22 are [−1600, 0].

Figure 23:
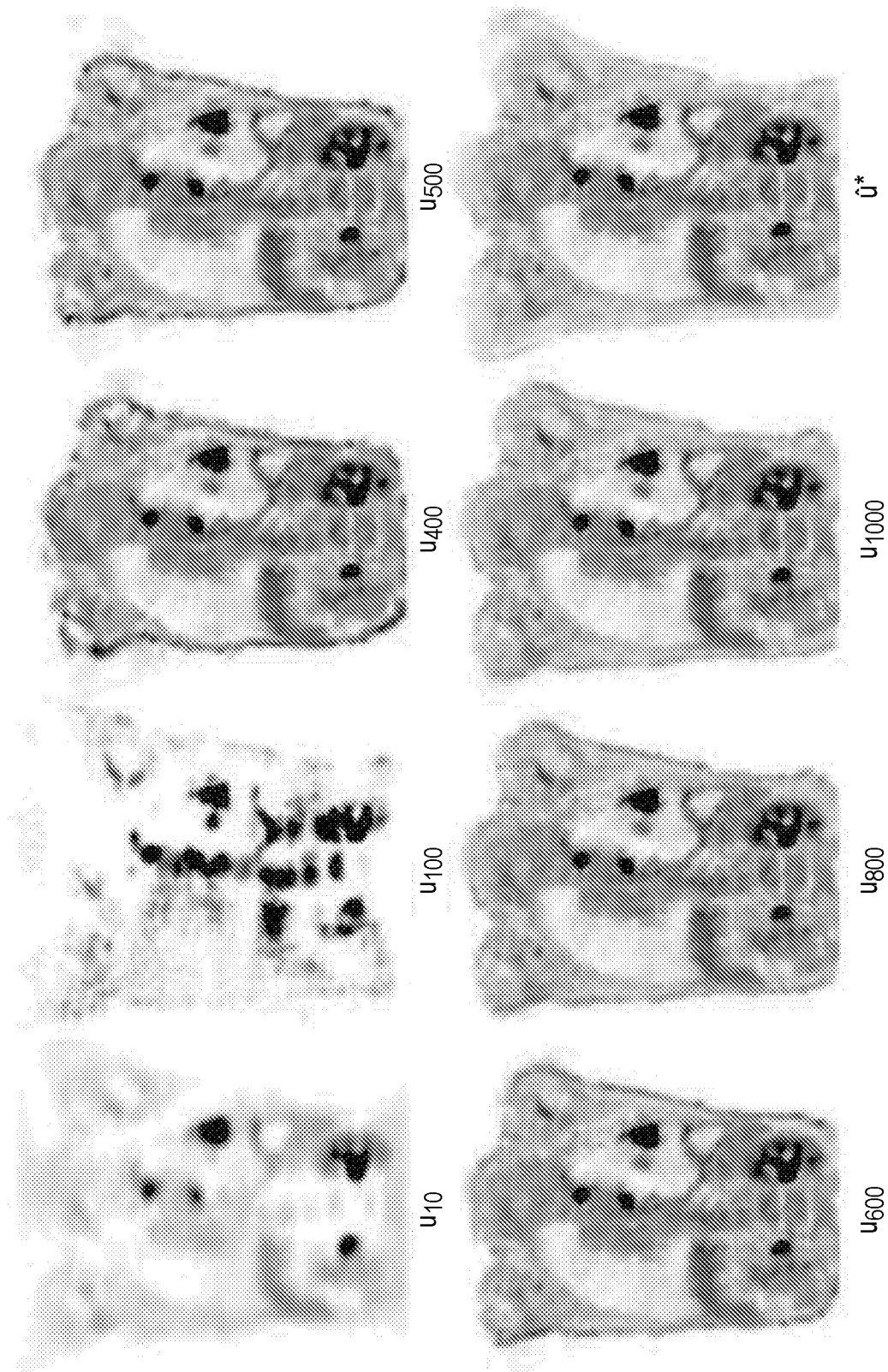

Reconstruction of the human images as a function of the number of iterations was next considered. Reconstructions of the human images were obtained again when the practical convergence conditions in Equation (13) are satisfied. We also investigated how the summed reconstruction of the human subject evolves as a function of the iteration number. To illustrate, FIG. 23 shows negative reconstructions $u_n$ at iteration n=10, 100, 400, 500, 600, 800, and 1000, along with negative final-convergent reconstruction $\hat{u}^*$, within a coronal slice of the human subject obtained from full data of all bed positions with optimization program DKL-fTV. The display windows are [−1600, 0]. It can be observed that the reconstruction at, e.g., about iteration 600, visually resembles the convergent reconstruction. Similar observations can also be made for reconstructions obtained from sparse data of the human subject (not shown).

In a human subject, the scatter component $g_s$ with attenuation-effect correction, is a program parameter that can be estimated from experimental measurements. The degree of estimation variability of $g_s$ can impact the reconstruction. To inspect the impact, we repeated the DKL-fTV reconstruction from full data of the human subject at bed position 3. Using $g_s$ obtained experimentally at bed position 3, we created hypothetically under- and over-estimated scatter events by scaling $g_s$ with a factor ranging from 0 to 2.

Figure 24:
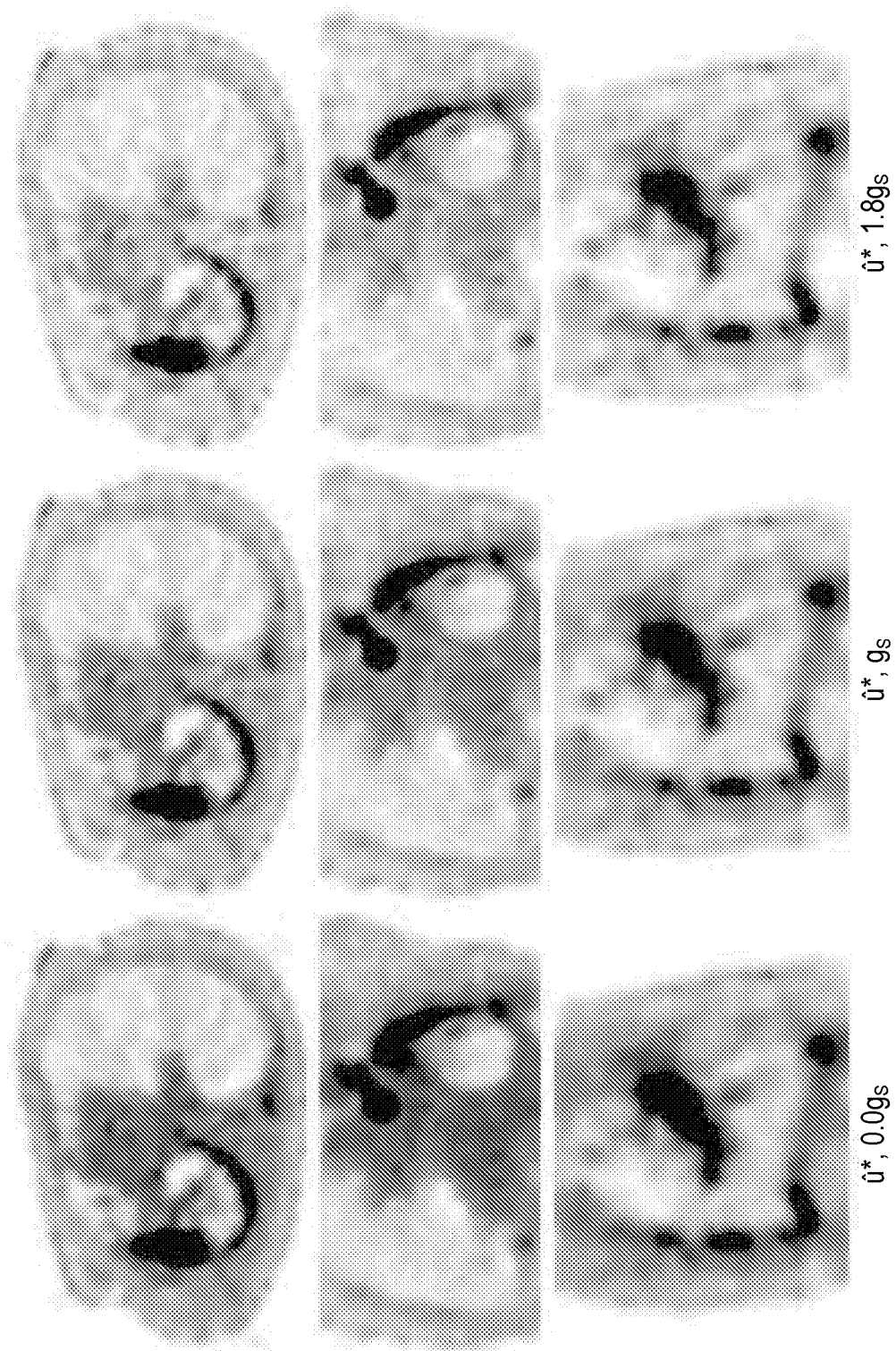

FIG. 24 shows negative convergent reconstructions $\hat{u}^*$ within a transverse slice (row 1), a coronal slice (row 2), and a sagittal slice (row 3) of the human subject obtained with program DKL-fTV from full data at bed position 3 corrected for scatter events by use of $0.0g_s$ (left column), $g_s$ (middle column), and $1.8g_s$ (right column), respectively. In FIG. 24 the display windows are [−1600, 0]. The visual difference among these images indicates the effect of different estimates of the scatter events on the reconstruction. The study can conversely be exploited for fine-tuning the estimate of the scatter events for yielding desired reconstructions.

Data collected in PET imaging generally have signal-to-noise ratio (SNR) considerably lower than that of data in typical computed tomography (CT) imaging. This is a consequence of the low radioactivity of a radiopharmaceutical administered to a patient for PET imaging, compared with the much higher permissible x-ray beam flux commonly used in clinical CT imaging. Furthermore, transitions among different uptake regions or other clinically salient features in a PET-activity map are commonly observed to be generally not as sharp as transitions among anatomic regions in a CT image. This is a consequence of the typical spread distribution of radiopharmaceutical in organs and tissue, i.e. the radiopharmaceutical is not entirely contained within the organ or tissue of interest but rather its concentration is higher (by design of the radiopharmaceutical) in the organ or tissue of interest compared with surrounding tissue.

To accommodate these significant differences as compared with CT, it is disclosed herein to formulate the optimization program (Equation (2)) with the PET image u represented as a product of a latent image f and a Gaussian blurring matrix or blurring operator $\mathcal{G}$, as shown in Equation (3). This formulation allows for a latent image with sparser gradient magnitude image than the desired image, and avoids yielding an image with significant patchy textures for PET data with low SNR. Further, as seen in the optimization program of Equation (2) a limit on the image total variability is enforced as a constraint, rather than as a term of an objective function that is optimized thus separating out enforcement of the total variability limit from the optimization objective function.

As shown herein, the form of the optimization program itself can also significantly affect PET-image reconstruction. The studies reported here indicate that the optimization program DKL-fTV employing the Kullback-Leibler divergence (Equation (4)) yields reconstructions superior to those obtained with the other two programs investigated (Equations (5) and (6)). In addition to the program form, numerous parameters used for specification of a program can have a significant impact on the final reconstruction. Among the parameters of the optimization program, image-TV-constraint parameter $t_0$ was observed to strongly affect reconstruction properties.

Image reconstructions have been carried out in different studies involving objects with considerably distinct activity-uptake distributions of practical relevance and data with different quality/quantity conditions of interest. The results show that the reconstruction based upon program DKL-fTV appears to be robust for the different activity up-takes and data sets under consideration. Moreover, a study was conducted for image reconstruction from data collected (or simulated to be collected via extraction from the full data set) with a PET configuration containing only half of the detectors in a digital prototype PET/CT scanner (the sparse configuration of FIG. 1A). The study reveals the robustness of DKL-fTV reconstruction with respect to significantly different data conditions. Viewed in another way, this study shows that the DKL-fTV reconstruction enables PET-scanner configurations with various sparse detector distributions.

The use of image total variation (image TV) as a constraint has numerous advantages. As a constraint, the impact of the image TV on the image is readily understood it enforces an upper limit on the permissible total image variability. This can be seen, for example, by considering the limiting cases. If $t_0$ approaches zero then no image variability is permitted, resulting in a flat (i.e. perfectly smooth) image. By contrast, if $t_0$ becomes sufficiently large then the image variability constraint is effectively removed, as the constraint does not impact the image no matter how much image variability is present. In general, a smaller value of $t_0$ biases toward a smoother image, albeit at a possible loss of some detail; whereas, a larger value of $t_0$ biases toward improved image sharpness, albeit at a possible increase in overall image noise. However, unlike in the case of applying a post-reconstruction image smoothing filter, applying the image TV constraint during image reconstruction generally does not adversely impact overall image contrast.

Another advantage of using image TV as a constraint is that it is generally operable with other constraints, and the various constraints can be considered to be operating (at least approximately) independently. For example, in the optimization program examples of Equations (2) and (4)-(6), in addition to the TV constraint an additional positivity constraint is applied (the constraint $f_j \geq 0$).

While the illustrative image TV constraint is shown by experiments reported herein to provide enhanced image quality for both full and sparse data sets, in other embodiments another constraint performing analogous function could be used. For example, more generally a norm of a sparse gradient magnitude image could be used as a constraint in place of the illustrative image TV constraint. Even more generally, a norm of another image sparsifying image transform such as a wavelet, curvet, or Fourier transform could be used as the constraint. The generalized form of the image variability constraint may be written as $\|T(u)\| \leq t_0$, where u is the reconstructed image at a current iteration of the constrained optimization program, T(u) is the sparsifying image transform (e.g. wavelet, curvet, Fourier transform, et cetera) and outputs a transformed version of the image u, and $\| \ldots \|$ is a norm, i.e. a function that outputs a strictly positive scalar value for the transformed image T(u). In the example of Equations (2) and (3), $T(u) = f = \mathcal{G}^{-1}u$ and the norm $\| \ldots \|$ is the image total variability, i.e. $\| \ldots \|_{TV}$. (In the limiting case where $\mathcal{G}$ is the identity matrix, $T(u)=u$.) These constraints generally serve to constrain the maximum permissible image variability, albeit less directly than the illustrative image TV constraint. Note that in this generalized framework the positivity constraint $f_j \geq 0$ becomes $[T(u)]_j \geq 0$.

While the illustrative embodiments are directed to PET imaging, it will be appreciated that the disclosed image reconstruction techniques are readily applied to other types of emission imaging data, such as time-of-flight (TOF) PET imaging data or single photon emission computed tomography (SPECT) imaging data, with suitable adjustment of the model of Equation (1). In designing the reconstruction for such imaging data, the disclosed approaches for selecting and/or optimizing parameters of the optimization program (parameters and form, e.g. choice of divergence) are suitably performed to tailor the reconstruction.

The benefits of the disclosed image reconstruction with image variability constraint demonstrated for full and sparse PET data sets as per FIG. 1A are also expected to accrue for any type of incomplete emission data set, whether due to a sparse detector array (i.e. with missing elements compared with a full regular or two-dimensional period array), or due to a reduced number of views (e.g. SPECT step-and-shoot imaging with fewer steps), or so forth. In general, by constraining the image total variability the impact of artifacts due to incomplete sampling can be suppressed, but the image total variability constraint has less tendency to introduce new artifacts as compared with post-reconstruction image filters. Thus, benefits may be obtained such as reduced equipment cost due to a reduced number of detectors, and/or reduced imaging time due to acquisition over fewer views. The benefits are also expected to accrue for imaging with reduced total data quantity, for example due to reduced acquisition time and/or reduced radiopharmaceutical dosage.

In general, it is expected that performing an integrated design of both the sparse detector configuration (e.g., selecting the pattern, or randomness, of omitted detector elements) and the image reconstruction with image total variability constraint (selecting/optimizing the optimization program form and parameters) should yield improved performance for the overall system combination including the PET scanner (or SPECT gamma camera) with sparse detector array(s) and the image reconstruction algorithm. In this regard, it should be understood that the sparse detector array configuration 12S of FIG. 1A is merely an illustrative example, and that more generally the sparse array may be sparsified by omission of selected detector elements at various levels (e.g. tile, module) and in various chosen patterns (or lack of pattern, e.g. random omission of tiles and/or modules).

Yet another advantage of the disclosed approach employing iterative reconstruction with an image variability constraint is that the constraint can be tuned, or "dialed in" to accommodate run-to-run differences in imaging data, and/or to accommodate different clinical tasks that may benefit from different trade-offs between, on the one hand, highly smooth image texture (enforced with a lower maximum allowable image variability, e.g. lower $t_0$ in the illustrative optimization programs employing image TV); and, on the other hand, high image sharpness (obtained by a higher maximum allowable image variability that effectively relaxes the image variability constraint, e.g. higher $t_0$ in the illustrative optimization programs employing image TV).

Figure 25:
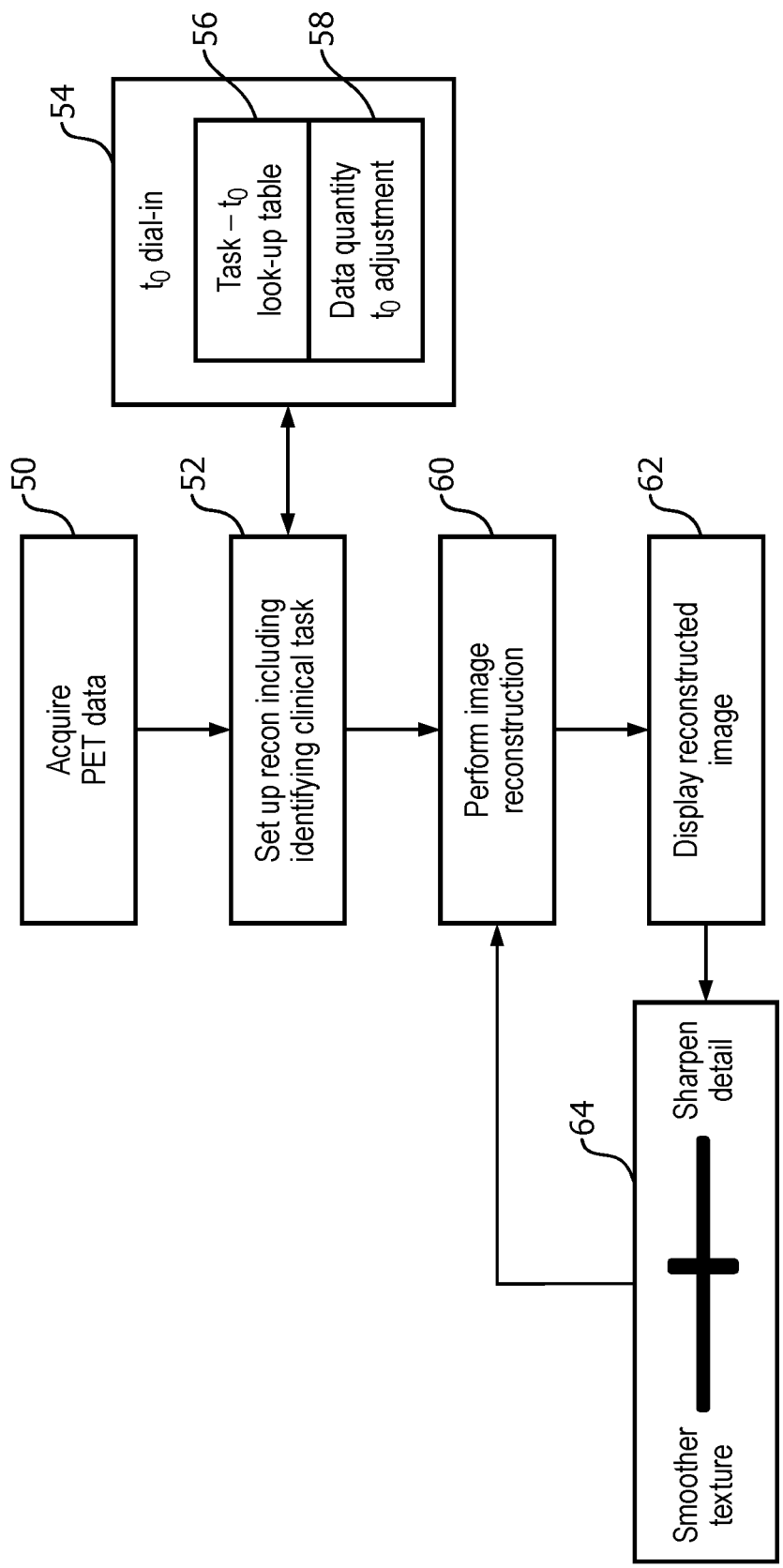
FIG. 25 illustrates a PET imaging method suitably performed using the PET imaging system of FIG. 1.

With reference to FIG. 25, an illustrative PET imaging method suitably performed using the PET imaging system of FIG. 1 is described. In an operation 50, PET imaging data are acquired, e.g. using the full scan configuration 12F or the sparse scan configuration 12S (see FIG. 1A). In an operation 52 the PET imaging system operator (e.g. a radiological technician or a radiologist) sets up the reconstruction. In some embodiments, this includes identifying the clinical task being performed. The set-up 52 makes reference to configuration look-up tables and/or formulas 54 to select parameters of the optimization program (and in some embodiments, also to select the form of the optimization program, e.g. the choice of divergence). In illustrative FIG. 25, only selection of the image TV constraint parameter $t_0$ is illustrated, so that $t_0$ dial-in tables and/or formulas are shown, but as just mentioned it is contemplated to have similar tables and/or formulas for dialing in other optimization parameters, and/or to select the program form. For example, in some embodiments the standard deviation or other parameter of the Gaussian blurring matrix or blurring operator $\mathcal{G}$ (Equation (3)) could be similarly dialed in.

The illustrative $t_0$ dial-in tables and/or formulas 54 include a task-$t_0$ look-up table 56 that includes (task, $t_0$) pairs. This look-up table 56 is suitably constructed by a skilled radiologist, for example, using the visual inspection approach described with reference to FIG. 17, but perhaps with the number of iterations limited to a reduced number typically used in clinical reconstruction tasks. Optionally, both $t_0$ and the number of iterations may be optimized in this way for various tasks, so that in this variant embodiment the look-up table 56 includes triplet entries of the form (task, $t_0$, n) where n is the number of iterations to be performed for a particular task. In another approach, a task-specific convergence criterion is substituted for n. The clinical tasks may be defined in various ways, such as by anatomical region, clinical objective(s), patient characteristics (age, gender, etc), or so forth.

The illustrative $t_0$ dial-in tables and/or formulas 54 further include a data quantity $t_0$ adjustment 56 that adjusts $t_0$ based on the quantity of acquired PET data. In general, if a large quantity of data is available (for example, due to a long imaging data acquisition time and/or high radiopharmaceutical dosage used in the operation 50) then the image TV constraint parameter $t_0$ is adjusted upward to impose a less aggressive constraint on the permissible image variability, in the expectation that the large data set should produce a correspondingly high quality reconstructed image without aggressive variability constraint. By contrast, if a small quantity of data is available (for example, due to a short imaging data acquisition time and/or low radiopharmaceutical dosage used in the operation 50) then the image TV constraint parameter $t_0$ is adjusted downward to impose a more aggressive constraint on the permissible image variability, in the expectation that the small data set may lead to large artifacts that should be countered by more aggressive constraint on the image total variability. The data quantity adjustment 56 may be implemented as a look-up table (e.g. assigning various $t_0$ values to different quantity range bins) or as an empirical formula, e.g. of the form $t_0=f(N)$ where N is a metric of the quantity of acquired PET data. In some embodiments the quantity adjustment 56 may be tied to the clinical task by integrating the adjustment 56 into the task look-up table 54 (e.g., having different data quantity adjustment formulas defined for different clinical tasks). While a quantity adjustment 56 is illustrated, other data set-specific $t_0$ adjustments may be similarly made, e.g. based on PET scanner configuration, the particular PET scanner that acquired the data set (in radiology laboratories having multiple PET scanners connected to a common reconstruction system) or so forth.

With continuing reference to FIG. 25, when the operator is satisfied with the reconstruction set-up then the reconstruction is initiated and performed in an operation 60 to generate a reconstructed image by executing the chosen optimization program (i.e. with the form and parameters chosen in the operation 52) to generate a reconstructed image that is displayed in an operation 62. In some contemplated embodiments, the operator is given the opportunity to adjust one or more reconstruction parameters based on visual assessment of the image displayed in the operation 62. As an illustrative example, an image adjustment slide bar 64 may be displayed via which the user may select for smoother texture (achievable by lowering $t_0$) or may select for sharpened detail (achievable by raising $t_0$). The limits on the range of $t_0$ achievable using the slide bar 64 may be variously defined, for example as a percentage of the value chosen in the set-up 52 (e.g. maximum smoothness ~80% of the original $t_0$ to maximum sharpness ~120% of the original $t_0$), or within a range pre-defined for the identified clinical task. Upon user selection of this change in $t_0$ via the slide bar 64, process flows back to the image reconstruction 60 to perform further iterations of the optimization program with the updated value for $t_0$, and the resulting updated image using the updated $t_0$ value is displayed in a second pass through the display operation 62. In this approach, the reconstructed image initially generated during the first pass through block 60 may be used as the initial image for the further iterations of the optimization program. It may be noted that the choice of user interface dialog for modifying $t_0$ may be other than the illustrative slide bar. Further, as in the illustrative embodiment the user interface dialog does not necessarily explicitly identify that $t_0$ is the parameter being adjusted (e.g., illustrative slide bar 64 is labeled with the "smoother texture" and "sharpen detail" labels).

APPENDIX—IEC PHANTOM AND ASSOCIATED METRICS

Figure 26:
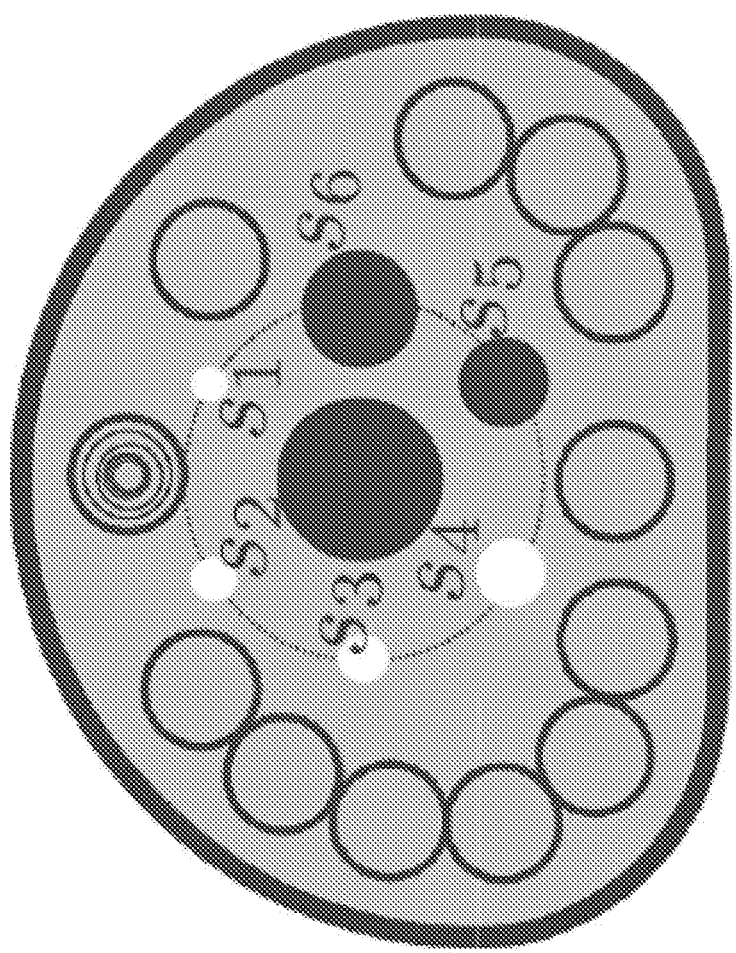
FIG. 26 diagrammatically shows an IEC phantom used in some studies presented herein.

FIG. 26 illustrates a transverse slice of the IEC (International Electrotechnical Commission) phantom used in the IEC phantom studies. In this phantom, six spheres labeled in FIG. 26 as $s_1$, $s_2$, $s_3$, $s_4$, $s_5$, and $s_6$, respectively, are embedded within the background and have diameters of 10, 13, 17, 22, 28, and 37 mm, respectively. Spheres $s_1$-$s_4$, referred to hot spheres, have an identical concentration level of positron emitters, which is four times of that in the background. Spheres $s_5$ and $s_6$, referred to as cold spheres, contain no positron emitters. The dark circle at the center displays a transverse cross-section of the cylinder containing zero activity in the phantom. Additionally, twelve identical circular background regions of interest (ROIs) of diameter 37 mm are drawn in the slice, as shown in FIG. 26, and also in each of its four nearest neighboring slices, thus amounting to a total of 60 background ROIs. Within each ROI, 6 sub-ROIs of sizes corresponding to those of the hot and cold spheres are also drawn, as indicated in the top ROI in FIG. 26, and thus a total of T=60 sub-ROIs for each of the sphere sizes is obtained, which are used below for calculating the average background activity for the corresponding sphere.

Using $C_{B,t,k}$ to denote the average background activity within sub-ROI t of the size of sphere k, we define an average background activity corresponding to sphere k as $C_{B,k} = \Sigma_{t=1}^{T} C_{B,t,k}$. With this, percent contrasts $Q_{H,j}$ and $Q_{C,i}$ for hot sphere j, where j=1, 2, 3, and 4, and cold sphere i, where i=5 and 6, and background variability $N_k$ for sphere k, where k=1, 2, 3, 4, 5 and 6, defined in NEMA NU 2-2012, are calculated as:

$$Q_{H,j} = \frac{C_{H,j} - C_{B,j}}{a_H - a_B} \times 100\% \tag{16}$$

and $$Q_{C,j} = \left(1 - \frac{C_{C,i}}{C_{B,i}}\right) \times 100\% \tag{17}$$

and $$N_k = \frac{\sqrt{\sum_{t=1}^{T}(C_{B,t,k} - C_{B,k})^2 / (T-1)}}{C_{B,k}} \times 100\% \tag{18}$$

where $a_H$ and $a_B$ denote truth activity concentrations in a hot sphere and background, $a_H = 4 \times a_B$, and $C_{H,j}$ and $C_{C,i}$ are the average activities within hot sphere j and cold sphere i.

We define a metric, which takes into account the trade-off between contrast and background noise, as:

$$QNR = \frac{Q_{H,2}}{N_2} \frac{Q_{C,5}}{N_5} \tag{19}$$

where $Q_{H,2}$ and $Q_{C,5}$ denote percent contrasts for hot sphere $s_2$ of diameter 13 mm and for cold sphere $s_5$ of diameter 28 mm, and $N_2$ and $N_5$ percent background variabilities corresponding to the two spheres.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An emission imaging device comprising:
   an emission imaging scanner including radiation detectors for acquiring emission imaging data;
   an electronic data processing device programmed to reconstruct emission imaging data acquired by the emission imaging scanner to generate a reconstructed image by executing a constrained optimization program that is constrained by an image variability constraint $\|T(u)\| \leq t_0$ in which $t_0$ is an image variability constraint parameter, u is the reconstructed image at a current iteration of the constrained optimization program, T(u) is a sparsifying image transform, and $\| \ldots \|$ is a norm that outputs a strictly positive scalar value for the transformed image T(u), wherein the norm $\| \ldots \|$ is the image total variation norm $\| \ldots \|_{TV}$; and
   a display device connected to display the reconstructed image.

2. The emission imaging device of claim 1 wherein the sparsifying image transform is T(u) is a wavelet, curvet, or Fourier transform.

3. The emission imaging device of claim 1 wherein the sparsifying image transform is $T(u) = \mathcal{G}_s^{-1} u$ where $\mathcal{G}_s$ is a Gaussian blurring matrix.

4. The emission imaging device of claim 1 wherein the image variability constraint is an image total variation constraint $\|f\|_{TV} \leq t_0$ in which $t_0$ is a total variation constraint parameter and f is a latent image defined by $u = \mathcal{G}_s f$ where $\mathcal{G}_s$ is a Gaussian blurring matrix which is not an identity matrix.

5. The emission imaging device of claim 3 wherein the Gaussian blurring matrix $\mathcal{G}_s$ is defined by a Gaussian function whose unit of standard deviation is defined in terms of image voxel size.

6. The emission imaging device of claim 1 wherein the constrained optimization program has the form:

$$u^* = \underset{u}{\operatorname{argmin}}\ D(g_m, g(u))\ \text{subject to}\ \|T(u)\| \leq t_0\ \text{and}\ [T(u)]_j \geq 0$$

where $g_m$ denotes the emission imaging data, g(u) denotes a data model of the emission imaging scanner that transforms the reconstructed image u at the current iteration of the constrained optimization program into emission imaging data, $D(g_m,g(u))$ denotes a measure of data fidelity between the $g_m$ and g(u), and $[T(u)]_j \geq 0$ is a positivity constraint.

7. The emission imaging device of claim 1 wherein the constrained optimization program has the form:

$$u^* = \underset{u}{\mathrm{argmin}} D(g_m, g(u)) \text{ subject to } \|f\|_{TV} \leq t_0 \text{ and } f_j \geq 0$$

where $g_m$ denotes the emission imaging data, g(u) denotes a data model of the emission imaging scanner that transforms the reconstructed image u at the current iteration of the constrained optimization program into emission imaging data, $D(g_m,g(u))$ denotes a measure of data fidelity between the $g_m$ and g(u), $\|f\|_{TV} \leq t_0$ is an image total variation constraint in which $t_0$ is a total variation constraint parameter, f is a latent image defined by $u=\mathcal{G}, f$ where $\mathcal{G}$, is a Gaussian blurring matrix which is not an identity matrix, and $f_j \geq 0$ is a positivity constraint.

8. The emission imaging device of claim 6 wherein $D(g_m,g(u))$ is the Kullback-Leibler (KL) divergence.

9. The emission imaging device of claim 1 wherein the emission imaging scanner is a positron emission tomography (PET) scanner, a time-of-flight positron emission tomography (TOF-PET) scanner, or a single photon emission computed tomography (SPECT) gamma camera.

10. The emission imaging device of claim 1 wherein the emission imaging scanner is a positron emission tomography (PET) scanner including an annular ring of PET radiation detectors, and the emission imaging data comprise line of response (LOR) data.

11. The emission imaging device of claim 1 wherein the electronic data processing device is further programmed to set up the constrained optimization program prior to its execution including selecting the image variability constraint parameter $t_0$ at least in part using a look-up table associating different values for $t_0$ to different clinical tasks.

12. The emission imaging device of claim 1 wherein the electronic data processing device is further programmed to set up the constrained optimization program prior to its execution including selecting the image variability constraint parameter $t_0$ at least in part based on a data quantity of the acquired emission imaging data.

13. An emission imaging method comprising:
acquiring emission imaging data $g_m$ for a subject using an emission imaging scanner including radiation detectors;
reconstructing the emission imaging data to generate a reconstructed image by executing the optimization program:

$$u^* = \underset{u}{\mathrm{argmin}} D(g_m, g(u))$$

where g(u) denotes a data model of the emission imaging scanner that transforms the reconstructed image u at the current iteration of the optimization program into emission imaging data and $D(g_m,g(u))$ denotes a measure of data fidelity between the $g_m$ and g(u);
during the reconstructing, constraining each iteration of the optimization program by an image variability constraint $\|T(u)\| \leq t_0$ in which $t_0$ is an image variability constraint parameter, T(u) is a sparsifying image transform, and $\| \ldots \|$ is a norm that outputs a strictly positive scalar value for the transformed image T(u), wherein the norm $\| \ldots \|$ is the image total variation norm $\| \ldots \|_{TV}$; and
displaying the reconstructed image on a display device.

14. The emission imaging method of claim 13 further comprising:
during the reconstructing, further constraining each iteration of the optimization program by the positivity constraint $[T(u)]_j \geq 0$.

15. The emission imaging method of claim 13 wherein $D(g_m,g(u))$ is a Kullback-Leibler (KL) divergence.

16. The emission imaging method of claim 13 further comprising:
after the displaying, receiving a user input indicating an updated value for the image variability constraint parameter $t_0$;
executing further iterations of the optimization program to generate an updated reconstructed image with each further iteration of the optimization program constrained by the image variability constraint $\|T(u)\| \leq t_0$ using the updated value for the image variability constraint parameter $t_0$; and
displaying the updated reconstructed image on the display device.

17. A positron emission tomography (PET) imaging device comprising:
a PET scanner including an annular ring of radiation detectors for acquiring PET imaging data;
an electronic data processing device programmed to reconstruct PET imaging data acquired by the PET scanner to generate a reconstructed image by executing a constrained optimization program:

$$u^* = \underset{u}{\mathrm{argmin}} D(g_m, g(u)) \text{ subject to } \|f\|_{TV} \leq t_0 \text{ and } f_j \geq 0$$

where g(u) denotes a data model of the PET scanner that transforms the reconstructed image u at the current iteration of the constrained optimization program into emission imaging data, $D g_m,g(u))$ denotes a measure of data fidelity between the $g_m$ and g(u), $\|f\|_{TV} \leq t_0$ is an image total variation constraint in which $t_0$ is a total variation constraint parameter and f is a latent image defined by $u=\mathcal{G}, f$ where $\mathcal{G}$, is a blurring matrix which is not an identity matrix, and $f_j \geq 0$ is a positivity constraint; and
a display device connected to display the reconstructed image.

18. The PET imaging device of claim 17 wherein the blurring matrix $\mathcal{G}$, is a Gaussian blurring matrix.

19. The PET imaging device of claim 18 wherein the Gaussian blurring matrix $\mathcal{G}$, is defined by a Gaussian function whose unit of standard deviation is defined in terms of image voxel size.

20. The PET imaging device of claim 17 wherein $D(g_m, g(u))$ is the Kullback-Leibler (KL) divergence.

21. The PET imaging device of claim 17 wherein the PET scanner is a time-of-flight (TOF) PET scanner and the electronic data processing device is programmed to reconstruct TOF-PET imaging data acquired by the TOF-PET scanner to generate the reconstructed image.

22. The PET imaging device of claim 17 wherein the annular ring of radiation detectors of the PET scanner has a sparse configuration in which some detectors of a regular pattern of detectors are omitted.

23. The PET imaging device of claim 17 wherein the electronic data processing device is further programmed to set up the constrained optimization program prior to its execution including selecting the total variation constraint parameter $t_0$ at least in part using a look-up table associating different values for $t_0$ to different clinical tasks.

24. The PET imaging device of claim 17 wherein the electronic data processing device is further programmed to set up the constrained optimization program prior to its execution including selecting the total variation constraint parameter $t_0$ at least in part based on a data quantity of the acquired PET imaging data.

* * * * *